United States Patent
O'Reilly et al.

(10) Patent No.: US 11,173,205 B2
(45) Date of Patent: Nov. 16, 2021

(54) METHODS OF SELECTING T CELL LINE AND DONOR THEREOF FOR ADOPTIVE CELLULAR THERAPY

(71) Applicant: Memorial Sloan Kettering Cancer Center, New York, NY (US)

(72) Inventors: Richard J. O'Reilly, Roxbury, CT (US); Ekaterina Doubrovina, Bronx, NY (US); Guenther Koehne, New York, NY (US); Aisha N. Hasan, Blue Bell, PA (US); Susan E. Prockop, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 589 days.

(21) Appl. No.: 15/523,544

(22) PCT Filed: Nov. 4, 2015

(86) PCT No.: PCT/US2015/058939
§ 371 (c)(1),
(2) Date: May 1, 2017

(87) PCT Pub. No.: WO2016/073550
PCT Pub. Date: May 12, 2016

(65) Prior Publication Data
US 2017/0319683 A1 Nov. 9, 2017

Related U.S. Application Data

(60) Provisional application No. 62/075,856, filed on Nov. 5, 2014.

(51) Int. Cl.
| | | |
|---|---|---|
| *G01N 33/50* | (2006.01) | |
| *G01N 33/574* | (2006.01) | |
| *A61K 35/17* | (2015.01) | |
| *A61K 39/00* | (2006.01) | |
| *A61K 39/25* | (2006.01) | |
| *G16B 35/00* | (2019.01) | |
| *G16B 45/00* | (2019.01) | |
| *G16C 20/60* | (2019.01) | |
| *G16B 35/20* | (2019.01) | |
| *C12Q 1/6881* | (2018.01) | |

(52) U.S. Cl.
CPC ............... *A61K 39/25* (2013.01); *A61K 35/17* (2013.01); *A61K 39/0011* (2013.01); *A61K 39/001153* (2018.08); *C12Q 1/6881* (2013.01); *G01N 33/505* (2013.01); *G01N 33/574* (2013.01); *G01N 33/57407* (2013.01); *G16B 35/00* (2019.02); *G16B 35/20* (2019.02); *G16B 45/00* (2019.02); *G16C 20/60* (2019.02); *A61K 2039/5158* (2013.01); *A61K 2039/572* (2013.01); *C12Q 2600/136* (2013.01); *C12Q 2600/172* (2013.01); *G01N 2333/03* (2013.01); *G01N 2333/045* (2013.01); *G01N 2333/05* (2013.01)

(58) Field of Classification Search
CPC ........... G01N 33/574; G01N 33/57407; G01N 33/505; G01N 2333/045; G01N 2333/05
See application file for complete search history.

(56) References Cited

U.S. PATENT DOCUMENTS

| | | | |
|---|---|---|---|
| 6,723,695 | B1 | 4/2004 | Burrows et al. |
| 8,425,898 | B2 | 4/2013 | Sampson et al. |
| 9,011,835 | B2 | 4/2015 | Sampson et al. |
| 2004/0265325 | A1 | 12/2004 | Diamond et al. |
| 2005/0181459 | A1 | 8/2005 | Baker et al. |
| 2014/0086888 | A1 | 3/2014 | Heslop et al. |

FOREIGN PATENT DOCUMENTS

| | | |
|---|---|---|
| CL | 199702140 | 10/1997 |
| CL | 199802108 | 8/1998 |
| CL | 199802417 | 10/1998 |
| CL | 201701110 | 1/2018 |
| JP | 2013/541332 A | 11/2013 |
| RU | 2003/127388 A | 2/2005 |
| WO | WO 1996/029394 | 9/1996 |
| WO | WO 1998/016238 | 4/1998 |
| WO | WO 1999/018981 | 4/1999 |
| WO | WO 2002/069232 A2 | 6/2002 |
| WO | WO 2002/069232 | 9/2002 |
| WO | WO 2011/017151 | 2/2011 |
| WO | WO 2012/038055 A1 | 3/2012 |
| WO | WO 2016/073550 | 5/2016 |
| WO | WO 2019/178170 | 9/2019 |

OTHER PUBLICATIONS

Hasan, Blood 122.21, Oct. 21, 2013, abstract (Year: 2013).*
HLA Nomenclature 2015 (Year: 2015).*
Heslop et al., Feb. 2010, "Long-term outcome of EBV-specific T-cell infusions to prevent or treat EBV-related lymphoproliferative disease in transplant recipients," Blood, 115(5):925-935 (Published online Oct. 30, 2009).
Prockop et al., 2015, "Successful treatment of refractory CMV chorioretinitis and meningoencephalitis with adoptive transfer of third party CMVpp65 specific T-cell lines," meeting abstract for the 57th American Society of Hematology (ASH) Annual Meeting and Exposition held in Orlando, Florida, Dec. 5-8, 2015, first published online on Nov. 5, 2015.

(Continued)

*Primary Examiner* — Michael Szperka
*Assistant Examiner* — Marianne DiBrino
(74) *Attorney, Agent, or Firm* — Jones Day

(57) ABSTRACT

Disclosed herein are methods of selecting an allogeneic T cell line for therapeutic administration to a patient having or suspected of having a pathogen or cancer. Also disclosed are methods of selecting a donor from whom to derive an allogeneic T cell line for therapeutic administration to a patient having or suspected of having a pathogen or cancer.

17 Claims, 1 Drawing Sheet

(56) References Cited

OTHER PUBLICATIONS

Rooney et al., Jan. 1995, "Use of gene-modified virus-specific T lymphocytes to control Epstein-Barr-virus-related lymphoproliferation," Lancet, 345(8941):9-13.
Balduzzi et al., Jul. 2011, "Polyomavirus JC-targeted T-cell therapy for progressive multiple leukoencephalopathy in a hematopoietic cell transplantation recipient," Bone Marrow Transplantation, 46(7):987-992.
Bao et al., Apr. 2012, "Adoptive immunotherapy with CMV specific cytotoxic T lymphocytes for stem cell transplant patients with refractory CMV infections," Journal of Immunotherapy, 35(3):293-298.
Blyth et al., Nov. 2011, "BK virus-specific T cells for use in cellular therapy show specificity to multiple antigens and polyfunctional cytokine responses," Transplantation, 92(10):1077-1084.
Burns and Crawford, Sep. 2004, "Epstein-Barr virus-specific cytotoxic T-lymphocytes for adoptive immunotherapy of post-transplant lymphoproliferative disease," Blood Reviews, 18(3):193-209.
Cortivo et al., Nov. 2012, "Anti CMV and/or anti adenovirus IFN-g-positive CD4+ CD8+ T lymphocytes for treatment of viral infections after allogeneic HSC transplantation: first results," Blood, 120(21):1906.
Einsele et al., Jun. 2002, "Infusion of cytomegalovirus (CMV)-specific T cells for the treatment of CMV infection not responding to antiviral chemotherapy," Blood, 99(11):3916-3922.
Eiz-Vesper et al., Jan. 2013, "Adoptive T-cell immunotherapy from third-party donors: characterization of donors and set up of a T-cell donor registry," Frontiers in Immunology, 3:410.
Feuchtinger et al., Nov. 2010, "Adoptive transfer of pp65-specific T cells for the treatment of chemorefractory cytomegalovirus disease or reactivation after haploidentical and matched unrelated stem cell transplantation," Blood, 116(20):4360-4367 (Published online Jul. 12, 2010).
Gahn et al., Jan. 2002, "Immunotherapy to reconstitute immunity to DNA viruses," Seminars in Hematology, 39(1):41-47.
Gerdemann et al., Jan. 2013, "Immunotherapeutic strategies to prevent and treat human herpesvirus 6 reactivation after allogeneic stem cell transplantation," Blood, 121(1):207-218.
Haque et al., Oct. 2011, "Complete regression of posttransplant lymphoproliferative disease using partially HLA-matched Epstein Barr virus-specific cytotoxic T cells," Transplantation,72(8): 1399-1402.
Haque et al., Aug. 2007, "Allogeneic cytotoxic T-cell therapy for EBV-positive posttransplantation lymphoproliferative disease: results of a phase 2 multicenter clinical trial," Blood, 110(4):1123-1131 (Published online Apr. 27, 2007).
Haque et al., Aug. 2002, "Treatment of Epstein-Barr-virus-positive post-transplantation lymphoproliferative disease with partly HLA-matched allogeneic cytotoxic T cells," Lancet, 360(9331):436-442.
Holmes-Liew et al., Mar. 2015, "Adoptive T-cell immunotherapy for ganciclovir-resistant CMV disease after lung transplantation," Clinical & Translational Immunology, 4(3):e35.
Kawakami et al., Oct. 2005, "A case of immune recovery vitritis induced by donor leukocyte infusion for the treatment of cytomegalovirus retinitis," European Journal of Haematology, 75(4):352-354.
Leen et al, Jun. 2013, "Multicenter study of banked third-party virus-specific T cells to treat severe viral infections after hematopoietic stem cell transplantation," Blood, 121(26):5113-5123 (Published online Apr. 22, 2013).
Leen et al., Oct. 2006, "Monoculture-derived T lymphocytes specific for multiple viruses expand and produce clinically relevant effects in immunocompromised individuals," Nature Medicine, 12(10):1160-1166 (Published online Sep. 24, 2006).
Louis et al., Nov.-Dec. 2010, "Adoptive transfer of EBV-specific T cells results in sustained clinical responses in patients with locoregional nasopharyngeal carcinoma," Journal of Immunotherapy, 33(9):983-990.
Papadopoulou et al., Jun. 2014, "Activity of broad-spectrum T cells as treatment for AdV, EBV, CMV, BKV, and HHV6 infections after HSCT," Science Translational Medicine, 6(242):242ra83.
Qasim et al., May 2013, "Interferon-γ capture T cell therapy for persistent Adenoviraemia following allogeneic haematopoietic stem cell transplantation," British Journal of Haematology, 161(3):449-452 (Published online Feb. 22, 2013).
Ramos et al., Jan. 2013, "Human papillomavirus type 16 E6/E7-specific cytotoxic T lymphocytes for adoptive immunotherapy of HPV-associated malignancies," Journal of Immunotherapy, 36(1):66-76.
Sili et al., Jan. 2012, "Production of good manufacturing practice-grade cytotoxic T lymphocytes specific for Epstein-Barr virus, cytomegalovirus and adenovirus to prevent or treat viral infections post-allogeneic hematopoietic stem cell transplant," Cytotherapy, 14(1):7-11.
Straathof et al., Mar. 2005, "Treatment of nasopharyngeal carcinoma with Epstein-Barr virus—specific T lymphocytes," Blood, 105(5):1898-1904 (Published online Nov. 12, 2004).
Sukdolak et al., Oct. 2013, "CMV-, EBV- and ADV-specific T cell immunity: screening and monitoring of potential third-party donors to improve post-transplantation outcome," Biology of Blood and Marrow Transplantation, 19(10):1480-1492 (Published online Jul. 23, 2013).
Uhlin et al., Oct. 2012, "Rapid salvage treatment with virus-specific T cells for therapy-resistant disease," Clinical Infectious Diseases, 55(8):1064-1073 (Published online Jul. 17, 2012).
Waldrop et al., Apr. 1997, "Determination of antigen-specific memory/effector CD4+ T cell frequencies by flow cytometry: evidence for a novel, antigen-specific homeostatic mechanism in HIV-associated immunodeficiency," Journal of Clinical Investigation, 99(7):1739-1750.
Walter et al., Oct. 1995, "Reconstitution of cellular immunity against cytomegalovirus in recipients of allogeneic bone marrow by transfer of T-cell clones from the donor," The New England Journal of Medicine, 333(16):1038-1044.
Wilkie et al., Jul.-Aug. 2004, "Establishment and characterization of a bank of cytotoxic T lymphocytes for immunotherapy of epstein-barr virus-associated diseases," Journal of Immunotherapy, 27(4):309-316.
Barker et al., Dec. 2010, "Successful treatment of EBV-associated posttransplantation lymphoma after cord blood transplantation using third-party EBV-specific cytotoxic T lymphocytes," Blood, 116(23):5045-5049 (Published online Sep. 8, 2010).
Doubrovina et al., Nov. 2007, "Leukemia-reactive cytotoxic CD8+ and CD4+ T-cells specific for novel WT-1 epitopes are generated in vitro by sensitization with overlapping pentadecapeptides (15-mers) spanning the wilms tumor protein," Blood, 110 (11).
Doubrovina et al., Mar. 2012, "Adoptive immunotherapy with unselected or EBV-specific T cells for biopsy-proven EBV+ lymphomas after allogeneic hematopoietic cell transplantation," Blood, 119(11):2644-2656 (Published online Dec. 2, 2011).
Doubrovina et al., Aug. 2012, "Mapping of novel peptides of WT-1 and presenting HLA alleles that induce epitope-specific HLA-restricted T cells with cytotoxic activity against WT-1(+) leukemias," Blood, 120(8):1633-1646 (Published online May 23, 2012).
Doubrovina et al., Nov. 2004, "In vitro stimulation with WT1 peptide-loaded Epstein-Barr virus-positive B cells elicits high frequencies of WT1 peptide-specific T cells with in vitro and in vivo tumoricidal activity," Clinical Cancer Research, 10(21):7207-7219.
Hasan et al., Dec. 2014, "Banked, GMP grade third party T-cell lines specific for CMVpp65 epitopes presented by certain prevalent HLA alleles more consistently clear CMV infections in a genetically heterogeneous population of HSCT recipients," Blood, 124(21):309.
Hasan et al., 2014, "Banked, GMP grade third party T-cell lines specific for CMVpp65 epitopes presented by certain prevalent HLA alleles more consistently clear CMV infections in a genetically heterogeneous population of HSCT recipients," meeting abstract for the 56th American Society of Hematology (ASH) Annual Meeting and Exposition held in San Francisco, California, Dec. 6-9, 2014, first published online on Nov. 6, 2014.
Hasan et al., Feb. 2014, "Generation and characterization of a third party GMP grade bank of CMV specific T-cells for adoptive

(56) References Cited

OTHER PUBLICATIONS immunotherapy of CMV infections in recipients of HSCT from cord blood or seronegative donors," Biology of Blood and Marrow Transplantation, 20(2):S131-S132.
Hasan et al., Nov. 15, 2013, "Generation and characterization of a third party GMP grade bank of CMV specific T-cells for adoptive immunotherapy of CMV infections in recipients of HSCT from cord blood or seronegative donors," Blood, 122(21):2021.
Hasan et al., Aug. 2009, "A panel of artificial APCs expressing prevalent HLA alleles permits generation of cytotoxic T cells specific for both dominant and subdominant viral epitopes for adoptive therapy," The Journal of Immunology, 183(4):2837-2850 (Published online Jul. 27, 2009).
Koehne et al., Jul. 2000, "Rapid selection of antigen-specific T lymphocytes by retroviral transduction," Blood, 96(1):109-117.
Koehne et al., Mar. 2002, "Quantitation, selection, and functional characterization of Epstein-Barr virus-specific and alloreactive T cells detected by intracellular interferon-gamma production and growth of cytotoxic precursors," Blood, 99(5):1730-1740.
Prockop et al., Dec. 2014, "Third party donor derived CMV specific T cells for the treatment of refractory CMV viremia and disease after hematopoietic stem cell transplant," Blood, 124(21):184.
Prockop et al., 2014, "Third party donor derived CMV specific T cells for the treatment of refractory CMV viremia and disease after hematopoietic stem cell transplant," meeting abstract for the 56th American Society of Hematology (ASH) Annual Meeting and Exposition held in San Francisco, California, Dec. 6-9, 2014, first published online on Nov. 6, 2014.
Prockop et al., Feb. 2014, "Third party donor derived EBV specific T cells for the treatment of refractory EBV-related post-transplant lymphomas," Biology of Blood and Marrow Transplantation, 20(2):S49-S50.
O'Reilly, meeting abstract for the oral presentation on Oct. 31, 2014 at The 76th Annual Meeting of the Japanese Society of Hematology, held Oct. 31-Nov. 2, 2014, Osaka, Japan.
Trivedi et al., Apr. 2005, "Generation of CMV-specific T lymphocytes using protein-spanning pools of pp65-derived overlapping pentadecapeptides for adoptive immunotherapy," Blood, 105(7):2793-2801 (Published online Oct. 28, 2004).
O'Reilly et al., Sep. 2011, "Novel strategies for adoptive therapy following HLA disparate transplants," Best Practice & Research Clinical Haematology, 24(3):381-391.
O'Reilly et al., May 2007, "Adoptive transfer of antigen-specific T-cells of donor type for immunotherapy of viral infections following allogeneic hematopoietic cell transplants," Immunologic Research, 38(1-3):237-250.
O'Reilly et al., Jun. 2010, "Adoptive transfer of unselected or leukemia-reactive T-cells in the treatment of relapse following allogeneic hematopoietic cell transplantation," Seminars in Immunology, 22(3):162-172 (Published online May 26, 2010).
"Biological therapy in treating patients at high-risk or with lymphoma, lymphoproliferative disease, or malignancies," ClinicalTrials.gov, accessed at https://clinicaltrials.gov/ct2/show/NCT00002663?term=NCT00002663&rank=1, first received on Nov. 1, 1999, accessed on Oct. 21, 2014, 5 pages.
"Therapeutic effects of Epstein-Barr virus immune T-lymphocytes derived from a normal HLA-compatible or partially-matched third-party donor in the treatment of EBV lymphoproliferative disorders and EBV-associated malignancies," ClinicalTrials.gov, accessed at http://www.clinicaltrials.gov/ct2/show/NCT01498484?term=NCT01498484&rank=1, first received on Dec. 21, 2011, accessed on Oct. 21, 2014, 5 pages.
"Primary transplant donor derived CMVpp65 specific T-cells for the treatment of CMV infection or persistent CMV viremia after allogeneic hematopoietic stem cell transplantation," ClinicalTrials.gov, accessed at http://www.clinicaltrials.gov/ct2/show/NCT01646645?term=NCT01646645&rank=1, first received on Jul. 18, 2012, accessed on Oct. 21, 2014, 4 pages.
"Trial of third party donor derived CMVpp65 specific T-cells for the treatment of CMV infection or persistent CMV viremia after allogeneic hematopoietic stem cell transplantation," ClinicalTrials.gov, accessed at https://clinicaltrials.gov/ct2/show/NCT02136797?term=NCT02136797&rank=1, first received on May 9, 2014, accessed on Nov. 10, 2014, 4 pages.
"Dose escalation trial of WT1-sensitized T cells for residual or relapsed leukemia after allogeneic hematopoietic progenitor cell transplantation," ClinicalTrials.gov, accessed at https://clinicaltrials.gov/ct2/show/NCT00620633?term=NCT00620633&rank=1, first received on Feb. 11, 2008, accessed on Oct. 3, 2016, 4 pages.
"Busulfan, melphalan, fludarabine and T-cell depleted allogeneic hematopoietic stem cell transplantation followed by post transplantation donor lymphocyte infusions," ClinicalTrials.gov, accessed at https://clinicaltrials.gov/ct2/show/NCT01131169?term=NCT01131169&rank=1, first received on May 25, 2010, accessed on Jan. 5, 2015, 5 pages.
"Dose escalation trial of WT-specific donor-derived T cells following -cell depleted allogeneic hematopoietic stem cell transplantation for patients with relapsed/refractory multiple myeloma," ClinicalTrials.gov, accessed at https://clinicaltrials.gov/ct2/show/NCT01758328?term=NCT01758328&rank=1, first received on Dec. 24, 2012, accessed on Oct. 3, 2016, 4 pages.
Prockop, "Adoptive immunotherapy with banked virus specific 3rd party donor T-cells for CMV infections and EBV LPD complicating hematopoietic cell transplants," slide presentation on Oct. 31, 2014 at the 76th Annual Meeting of the Japanese Society of Hematology, held Oct. 31-Nov. 2, 2014, Osaka, Japan, 43 pages.
Prockop, "Third party donor T cells for the treatment of CMV infection and EBV lymphoma in immunodeficient patients," slide presentation on May 22, 2014 at the 9th Meeting of the EBMT Pediatric Diseases WP, held May 21-23, 2014, Jerusalem, Israel, 47 pages.
Prockop, "3rd party CMV specific T cells for the treatment of refractory CMV viremia and disease after HSCT," slide presentation on Dec. 7, 2014 at the 56th ASH Annual Meeting held Dec. 6-9, 2014, San Francisco, California, United States, 27 pages.
Hasan, "Banked, GMP grade third party T-cell lines specific for CMVpp65 epitopes presented by certain prevalent HLA alleles more consistently clear CMV infections in a genetically heterogeneous population of HSCT recipients," slide presentation on Dec. 8, 2014 at the 56th ASH Annual Meeting held Dec. 6-9, 2014, San Francisco, California, United States, 22 pages.
Prockop, "Third party donor derived EBV specific T cells for the treatment of refractory lymphoma in immunodeficient recipients," slide presentation on Mar. 1, 2014 at the ASBMT 2014 BMT Tandem Meetings held Feb. 26-Mar. 2, 2014, Grapevine, Texas, United States, 22 pages.
Khanna et al., Aug. 1999, "Activation and adoptive transfer of Epstein-Barr virus-specific cytotoxic T cells in solid organ transplant patients with posttransplant lymphoproliferative disease," Proceedings of the National Academy of Sciences of the United States of America, 96(18):10391-10396.
Comoli et al., Apr. 2002, "Infusion of autologous Epstein-Barr virus (EBV)-specific cytotoxic T cells for prevention of EBV-related lymphoproliferative disorder in solid organ transplant recipients with evidence of active virus replication," Blood, 99(7):2592-2598.
Gandhi et al., May 2007, "Immunity, homing and efficacy of allogeneic adoptive immunotherapy for posttransplant lymphoproliferative disorders," American Journal of Transplantation, 7(5):1293-1299 (Published online Apr. 8, 2007).
Lucas et al., Mar. 1996, "The development of cellular immunity to Epstein-Barr virus after allogeneic bone marrow transplantation," Blood, 87(6):2594-2603.
Rooney et al., Sep. 1998, "Infusion of cytotoxic T cells for the prevention and treatment of Epstein-Barr virus-induced lymphoma in allogeneic transplant recipients," Blood, 92(5):1549-1555.
Schmitt et al., Mar. 2011, "Adoptive transfer and selective reconstitution of streptamer-selected cytomegalovirus-specific CD8+ T cells leads to virus clearance in patients after allogeneic peripheral blood stem cell transplantation," Transfusion, 51(3):591-599 (Published online Dec. 6, 2010).
Micklethwaite et al., Jun. 2007, "Ex vivo expansion and prophylactic infusion of CMV-pp65 peptide-specific cytotoxic T-lympho-

(56) References Cited

OTHER PUBLICATIONS cytes following allogeneic hematopoietic stem cell transplantation," Biology of Blood and Marrow Transplantation, 13(6):707-714 (Published Apr. 6, 2007).

Cobbold et al., Aug. 2005, "Adoptive transfer of cytomegalovirus-specific CTL to stem cell transplant patients after selection by HLA-peptide tetramers," The Journal of Experimental Medicine, 202(3):379-386.

Peggs et al., Oct. 2003, "Adoptive cellular therapy for early cytomegalovirus infection after allogeneic stem-cell transplantation with virus-specific T-cell lines," Lancet, 362(9393):1375-1377.

Latouch and Sadelain, Apr. 2000, "Induction of human cytotoxic T lymphocytes by artificial antigen-presenting cells," Nature Biotechnology, 18:405-409.

Amarnath and Fowler, Jan. 2012, "Harnessing autophagy for adoptive T cell therapy," Immunotherapy, 4(1):1-4.

Humar et al., Dec. 2009, "Cytomegalovirus in solid organ transplant recipients," American Journal of Transplantation, 9(Suppl 4):S78-S86.

International Search Report, Information on Search Strategy, and Written Opinion of the International Searching Authority, for International Patent Application No. PCT/US2015/058939, dated Feb. 10, 2016, 16 pages.

Saveanu et al., Oct. 2005, "Complexity, contradictions, and conundrums: studying post-proteasomal proteolysis in HLA class I antigen presentation," Immunological Review 207:42-59.

Strehl et al., Oct. 2005, "Interferon-gamma, the functional plasticity of the ubiquitin-proteasome system, and MHC class I antigen processing," Immunological Review 207:19-30.

Sercarz et al., 1993, "Dominance and crypticity of T cell antigenic determinants," Annual Review of Immunology, 11:729-766.

Yewdell and Bennink, 1999, "Immunodominance in major histocompatibility complex class I-restricted T lymphocyte responses," Annual Review of Immunology, 17:51-88.

La Gruta et al., Jan. 2006, "A virus-specific CD8+ T cell immunodominance hierarchy determined by antigen dose and precursor frequencies," Proceedings of the National Academy of Sciences of the United States of America, 103(4):994-999.

Cole et al., Nov. 1994, "The MHC class l-restricted T cell response to Sendai virus infection in C57BL/6 mice: a single immunodominant epitope elicits an extremely diverse repertoire of T cells," International Immunology, 6(11):1767-1775.

Kast et al., Mar. 1991, "Protection against lethal Sendai virus infection by in vivo priming of virus-specific cytotoxic T lymphocytes with a free synthetic peptide," Proceedings of the National Academy of Sciences of the United States of America, 88(6): 2283-2287.

Day et al., Jul. 2001, "Relative dominance of epitope-specific cytotoxic T-lymphocyte responses in human immunodeficiency virus type 1-infected persons with shared HLA alleles," Journal of Virology, 75(14):6279-6291.

Yu et al., Sep. 2002, "Consistent Patterns in the Development and Immunodominance of Human Immunodeficiency Virus Type 1 (HIV-1)-Specific CD8+ T-Cell Responses following Acute HIV-1 Infection," Journal of Virology, 76(17):8690-8701.

Lacey et al., Apr. 2003, "Relative dominance of HLA-B*07 restricted CD8+ T-lymphocyte immune responses to human cytomegalovirus pp65 in persons sharing HLA-A*02 and HLA-B*07 alleles," Human Immunology 64(4):440-452.

Falkenburg et al., Sep. 2011, "Allogeneic HLA-A*02-restricted WT1-specific T cells from mismatched donors are highly reactive but show off-target promiscuity," The Journal of Immunology 187(5):2824-2833.

\* cited by examiner

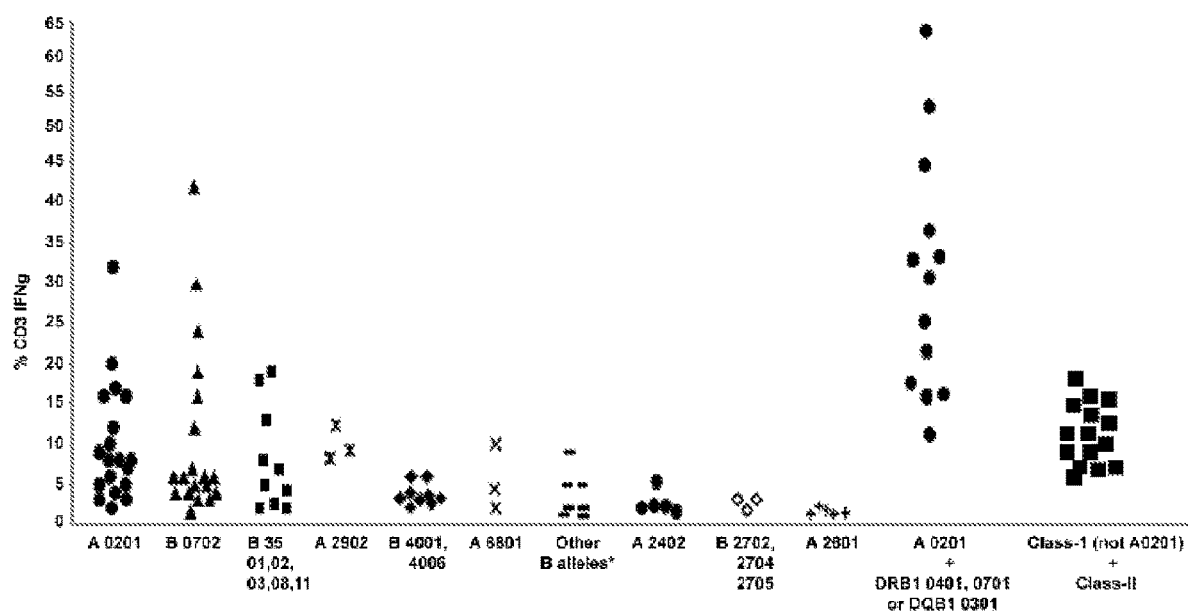

METHODS OF SELECTING T CELL LINE AND DONOR THEREOF FOR ADOPTIVE CELLULAR THERAPY

CROSS-REFERENCE TO RELATED APPLICATIONS

This application is a national stage of International Patent Application No. PCT/US2015/058939, filed Nov. 4, 2015, which claims the benefit of U.S. provisional application No. 62/075,856, filed on Nov. 5, 2014, each of which is incorporated by reference herein in its entirety.

GOVERNMENT RIGHTS STATEMENT

This invention was made with government support under CA023766, CA059350, CA008748, CA162002, CA106450, CA052477, and CA054350 awarded by National Institutes of Health. The government has certain rights in the invention.

1. FIELD

Disclosed herein are methods of selecting an allogeneic T cell line for therapeutic administration to a patient having or suspected of having a pathogen or cancer. Also disclosed are methods of selecting a donor from whom to derive an allogeneic T cell line for therapeutic administration to a patient having or suspected of having a pathogen or cancer.

2. BACKGROUND

Antiviral CD8+ T cells respond to a minute fraction of the potential peptide determinants encoded by viral genomes. Cytotoxic T-cells recognize infected cells through the interaction of the T-cell receptor (TCR) with 8-11-amino-acid antigenic peptides complexed with major histocompatibility (MHC) class-I molecules. These MHC-peptide complexes arise from intracellular processing of endogenously synthesized viral proteins (Saveanu, L., et al., Immunol Rev, 2005. 207: 42-59; Strehl, B., et al., Immunol Rev, 2005. 207: 19-30).

The peptide determinants conform to predicted binding motifs within specific HLA molecules. Although a large number of peptide epitopes may be generated, T-cell responses are focused to a selected number of epitopes, a phenomenon known as immunodominance (Sercarz, E. E., et al., Annu Rev Immunol, 1993. 11: 729-66; Yewdell, J. W. and J. R. Bennink, Annu Rev Immunol, 1999. 17: 51-88). The highly focused nature of CD8-T cell responses to pathogens indicates that individual epitopes differ in their capacity to induce T cell responses (Yewdell, J. W. and J. R. Bennink, Annu Rev Immunol, 1999. 17: 51-88).

Peptide epitopes that induce the most prominent T-cell responses in any given individual can be further classified based on the proportionate contribution of the epitope towards the overall T-cell response to any particular viral peptide. "Immunodominant" epitopes are recognized by the most abundant cognate T cell populations, whereas "subdominant" epitopes are recognized by less abundant T cell populations. Therefore, depending on their relative contributions to the total T cell response, individual epitopes can be classified as dominant, codominant, or subdominant, thereby establishing an immunodominance hierarchy.

In the case of influenza virus infection of mice, CD8 T cell responses are typically directed at only a handful of specific epitopes (La Gruta, N. L., et al., Proc Natl Acad Sci USA, 2006. 103: 994-999). And in a particularly extreme example, the entire CD8− T cell response to a mouse parainfluenza virus (Sendai virus) is directed at a single epitope (Cole, G. A. et al., Int Immunol, 1994. 6: 1767-1775; Kast, W. M., et al., Proc Natl Acad Sci USA, 1991. 88: 2283-2287).

Human T-cell responses have been characterized to several viral infections. Studies of T-cell responses against human immunodeficiency virus (HIV) have led to the identification of several epitopes in the various proteins of this virus, and these studies have also shown that the immunodominant epitopes can be presented by prevalent human leukocyte antigen (HLA) alleles such as HLA A0301, B0702 or A0201 within individuals co-inheriting these HLA alleles (Day, C. L., et al., J Virol, 2001. 75: 6279-6291). Furthermore, multiple epitopes can be presented by these same HLA alleles during different phases of the infection (Yu, X. G., et al., J Virol, 2002. 76: 8690-8701). Evaluation of T-cell responses against human cytomegalovirus (CMV) has led to the identification of several immunodominant epitopes within the most immunogenic proteins of this virus namely CMVpp65 and IE1, and their presenting HLA alleles. This then led to the recognition that among individuals inheriting specific HLA alleles, such as HLA B0702 and HLA A0201, the epitopes presented by these alleles constitute the immunodominant epitopes. When these alleles are co-inherited, epitopes presented by HLA B0702 constitute the immunodominant T-cell response while HLA A0201 presented epitopes are subdominant (Lacey, S. F., et al., Hum Immunol, 2003. 64: 440-452).

Immunodominance reflects the final product of a multitude of positive and negative factors that govern antigen processing and presentation as well as T cell activation and T-cell receptor avidity (Yewdell, J. W. and J. R. Bennink, Annu Rev Immunol, 1999. 17: 51-88). Among these, the main factors thus far evaluated in most studies have included the genetic HLA class-I background of the infected individuals, the sequence of viral proteins and kinetics of viral infections, as well as the binding affinities of the peptide epitopes in the HLA grooves as well as the TCR affinity to the peptide-MHC complex.

Adoptive immunotherapy using donor derived virus specific T-cells can be effective in eradicating viral infections such as Epstein-Barr virus (EBV) and CMV after allogeneic hematopoietic stem cell transplantation (HSCT). The lack of timely availability of donor derived virus specific T-cells has been a major limitation to the successful application of this treatment approach. Furthermore, such cells cannot be generated from seronegative and cord blood donors. In such cases, pre-generated third party donor derived virus specific T-cells could be readily available for treatment of serious viral infections in such patients. Several groups have demonstrated the safety and potential efficacy of third party donor derived virus specific cytotoxic T lymphocyte (CTL) lines for the treatment of EBV, CMV and adenovirus (ADV) infections, using CTL lines that were empirically infused based on matching for 2 or more HLA alleles (Hague, T, et al., Lancet, 2002. 360: 436-442; Barker, J. N., et al., Blood, 2010. 116: 5045-5049; Doubrovina, E., et al., Blood, 2012. 119: 2644-2656; Uhlin, M., et al., Clinical Infectious Diseases, 2012. 55: 1064-1073; Leen, A. M., et al., Blood, 2013. 121:5113-5123). There is a need for method of selecting CTL lines to ensure high and consistent efficacy of CTL treatment.

Citation of a reference herein shall not be construed as an admission that such is prior art to the present disclosure.

3. SUMMARY OF THE INVENTION

The present invention provides methods of selecting an allogeneic T cell line for therapeutic administration to a human patient having or suspected of having a pathogen or cancer, and methods of selecting an allogeneic T cell donor from whom to derive such an allogeneic T cell line.

In various aspects, the methods of selecting an allogeneic T cell line for therapeutic administration to a human patient having or suspected of having a pathogen or cancer comprise: selecting a T cell line allogeneic to the patient that recognizes at least one epitope of an antigen of the pathogen or the cancer, using a representation (hereinafter "Representation of Activity") that (i) identifies a plurality of HLA alleles and optionally HLA allele combinations, and (ii) discloses indications of relative activities of T cell lines, each recognizing at least one epitope of an antigen of the pathogen or cancer, and restricted to different ones of the HLA alleles or HLA allele combinations in the plurality; wherein in the representation each identified HLA allele or HLA allele combination is associated with the respective indication of relative activity of the T cell line restricted to the HLA allele or HLA allele combination, the relative activities being relative measures of known activity against the pathogen or against the cancer exhibited by the T cell lines; wherein (A) the T cell line selected has in common with the patient or diseased cells (e.g., of the cancer or associated with the presence of the pathogen) in the patient the HLA allele or HLA allele combination identified by the representation to which the recognition of the T cell line is restricted; and (B) the HLA allele or HLA allele combination, to which the T cell line selected is restricted, is associated in the representation with an indication of the highest relative activity among the HLA alleles and HLA allele combinations in the representation that are known to be in common with the patient or the diseased cells in the patient (based on the HLA assignment of the patient or the diseased cells in the patient) and are not otherwise disqualified.

In certain embodiments, the methods of selecting an allogeneic T cell line further comprise prior to the selecting step, a step of generating the Representation of Activity. In certain embodiments, the methods of selecting an allogeneic T cell line further comprise prior to the generating step, a step of measuring the relative activities. In certain embodiments, the methods of selecting an allogeneic T cell line further comprise prior to the selecting step, a step of ascertaining the HLA assignment of the patient or of the diseased cells in the patient. In specific embodiments, the step of ascertaining comprises typing at least 4 HLA loci.

In various aspects, the methods of selecting an allogeneic T cell donor from whom to derive an allogeneic T cell line for therapeutic administration to a human patient having or suspected of having a pathogen or cancer comprise: selecting a T cell donor allogeneic to the patient, using a Representation of Activity that (i) identifies a plurality of HLA alleles and optionally HLA allele combinations, and (ii) discloses indications of relative activities of T cell lines, each recognizing at least one epitope of an antigen of the pathogen or cancer, and restricted to different ones of the HLA alleles or HLA allele combinations in the plurality; wherein in the representation each identified HLA allele or HLA allele combination is associated with the respective indication of relative activity of the T cell line restricted to the HLA allele or HLA allele combination, the relative activities being relative measures of known activity against the pathogen or against the cancer exhibited by the T cell lines; wherein (A) the T cell donor selected has at least one HLA allele or HLA allele combination in common with the patient or diseased cells (e.g., of the cancer or associated with the presence of the pathogen) in the patient; and (B) one of the at least one HLA allele or HLA allele combination in common with the patient or the diseased cells in the patient is associated in the representation with an indication of the highest relative activity among the HLA alleles and HLA allele combinations in the Representation of Activity that are known to be in common with the patient or the diseased cells in the patient and are not otherwise disqualified.

In certain embodiments, the methods of selecting an allogeneic T cell donor further comprise prior to the selecting step, a step of generating the Representation of Activity. In certain embodiments, the methods of selecting an allogeneic T cell donor further comprise prior to the generating step, a step of measuring the relative activities. In certain embodiments, the methods of selecting an allogeneic T cell donor further comprise prior to the selecting step, a step of ascertaining the HLA assignment of the patient or the diseased cells in the patient. In certain embodiments, the methods of selecting an allogeneic T cell donor further comprise prior to the selecting step, a step of ascertaining the HLA assignment for the T cell donor. In certain embodiments, the methods of selecting an allogeneic T cell donor further comprise prior to the selecting step, a step of ascertaining the HLA assignment for the patient or the diseased cells in the patient and the HLA assignment for the T cell donor. In specific embodiments, the step of ascertaining comprises typing at least 4 HLA loci.

In some embodiments, the Representation of Activity is a list of the plurality of HLA alleles and optionally HLA allele combinations ranked by the relative activities. In some embodiments, the Representation of Activity is a database listing the plurality of HLA alleles and optionally HLA allele combinations, each associated with a score indicative of relative activity. In some embodiments, the Representation of Activity is a scatter plot. In a specific aspect of such embodiments, a first axis of the scatter plot represents different ones of the HLA alleles and optionally HLA allele combinations in the plurality, and a second axis of the scatter plot represents percentage of interferon-γ-secreting $CD3^+$ cells derived from each T cell line for which an indication of relative activity is disclosed in the representation, upon stimulation with antigen presenting cells that are autologous to the respective T cell line and are loaded with one or more peptides displaying the antigenicity of the pathogen or cancer, as the indication of said relative activity. In preferred embodiments, the relative activities are in vivo clinical efficacies of the T cell lines in treatment of patients having the pathogen or cancer. In some embodiments, the Representation of Activity is stored in a database.

In various aspects, the methods of selecting an allogeneic T cell donor from whom to derive an allogeneic T cell line for therapeutic administration to a human patient having or suspected of having a pathogen or cancer comprise: selecting a T cell donor allogeneic to the patient who has in common one or more HLA alleles with the patient or diseased cells (e.g., of the cancer or associated with the presence of the pathogen) in the patient, using a representation (hereinafter "Representation of Frequency") that (i) identifies a plurality of HLA alleles, and (ii) discloses indications of relative frequencies of generation of T cell lines, each recognizing at least one epitope of an antigen of the pathogen or the cancer, and restricted to different ones of said HLA alleles in the plurality; wherein in the representation each identified HLA allele is associated with the respective indication of relative frequency of generation of said T cell lines restricted to the HLA allele, wherein: the T cell donor selected has at least one HLA allele in common with the patient or the diseased cells in the patient that is associated in the representation with an indication of higher frequency of generation than HLA alleles of the donor that are not in common with the patient or the diseased cells in the patient.

In certain embodiments, the methods of selecting an allogeneic T cell donor further comprise prior to the selecting step, a step of generating the Representation of Frequency. In certain embodiments, the methods of selecting an allogeneic T cell donor further comprise prior to the generating step, a step of measuring the relative frequencies. In certain embodiments, the methods of selecting an allogeneic T cell donor further comprise prior to the selecting step, a step of ascertaining the HLA assignment for the patient or the diseased cells in the patient. In certain embodiments, the methods of selecting an allogeneic T cell donor further comprise prior to the selecting step, a step of ascertaining the HLA assignment for the T cell donor. In certain embodiments, the methods of selecting an allogeneic T cell donor further comprise prior to the selecting step, a step of ascertaining the HLA assignment for the patient or the diseased cells in the patient and the HLA assignment for the T cell donor. In specific embodiments, the step of ascertaining comprises typing at least 4 HLA loci.

In some embodiments, the Representation of Frequency is a list of the plurality of HLA alleles ranked by the relative frequencies. In some embodiments, the Representation of Frequency is a database listing the plurality of HLA alleles, each associated with a score indicative of relative frequency. In some embodiments, the Representation of Frequency is stored in a database.

Also provided herein are methods of treating a human patient having or suspected of having a pathogen or cancer, comprising: (a) selecting an allogeneic T cell line for therapeutic administration to the patient according to a method described in this disclosure; and (b) administering a population of T cells derived from the selected allogeneic T cell line to the patient.

Also described herein are methods of obtaining an allogeneic T cell line for therapeutic administration to a human patient having or suspected of having a pathogen or cancer, comprising: (a) selecting an allogeneic T cell donor according to a method of selecting an allogeneic T cell donor as described in this disclosure; and (b) deriving an allogeneic T cell line from the selected allogeneic T cell donor, which allogeneic T cell line recognizes at least one epitope of an antigen or the pathogen or cancer.

In various aspects, the patient has or is suspected of having a pathogen, wherein the T cell lines recognize at least one epitope of an antigen of the pathogen. In various embodiments, the pathogen is a virus, bacterium, fungus, helminth or protist. In certain embodiments, the pathogen is a virus.

In some embodiments, the virus is cytomegalovirus (CMV). In specific embodiments, the patient has or is suspected of having a CMV infection subsequent to the patient having undergone a HSCT. In specific embodiments, the antigen is CMV pp65. In specific embodiments, the antigen is CMV IE1.

In some embodiments, the virus is Epstein-Barr virus (EBV). In specific embodiments, the antigen is EBNA1, EBNA2, EBNA3A, EBNA3B, EBNA3C, LMP1, or LMP2.

In some embodiments, the virus is BKV, JCV, herpesvirus, adenovirus, human immunodeficiency virus, influenza virus, ebola virus, poxvirus, rhabdovirus, or paramyxovirus.

In some embodiments, the virus is human herpesvirus-6 (HHV-6) or human herpesvirus-8 (HHV-8).

In various aspects, the patient has or is suspected of having a cancer, wherein the T cell line recognizes at least one epitope of an antigen of the cancer. In some embodiments, the cancer is a cancer of the breast, lung, ovary, stomach, pancreas, larynx, esophagus, testes, liver, parotid, biliary tract, colon, rectum, cervix, uterus, endometrium, kidney, bladder, prostate, thyroid, brain or skin. In some embodiments, the cancer is a cancer of the blood. In specific embodiments, the cancer is a lymphoproliferative disorder.

In some embodiments, the cancer is WT1-positive cancer. In some embodiments, the antigen is WT1.

In some embodiments, the cancer is EBV-positive post-transplant lymphoproliferative disorder (EBV-PTLD). In specific embodiments, the antigen is EBNA1, EBNA2, EBNA3A, EBNA3B, or EBNA3C. In specific embodiments, the antigen is LMP1 or LMP2.

In some embodiments, the cancer is EBV-positive nasopharyngeal carcinoma. In specific embodiments, the antigen is EBNA1, LMP1, or LMP2.

In various embodiments, a method of selecting an allogeneic T cell line as described in this disclosure is computer-implemented. In various embodiments, a method of selecting an allogeneic T cell donor as described in this disclosure is computer-implemented.

Also provided herein is a computer system for selecting an allogeneic T cell line for therapeutic administration to a human patient having or suspected of having a pathogen or cancer, comprising: a central processing unit; a memory, couple to the central processing unit, the memory storing instructions for performing the steps of any method of selecting an allogeneic T cell line or any method of selecting an allogeneic T cell donor as described in this disclosure.

Also provided herein is a computer readable medium having computer-executable instructions for performing the steps of any method of selecting an allogeneic T cell line or any method of selecting an allogeneic T cell donor as described in this disclosure.

In various embodiments, the patient has been the recipient of a hematopoietic stem cell transplantation (HSCT). In specific embodiments, the HSCT is a bone marrow transplant, peripheral blood stem cell transplant, or cord blood transplant. In various embodiments, the patient has been the recipient of a solid organ transplant (SOT).

The patient referred to in this disclosure is a human patient.

4. BRIEF DESCRIPTION OF FIGURES

FIG. 1 is a representation that depicts the percentage of interferon-γ-secreting CD3+ cells for each T cell line in a bank of 119 CMV-specific CTL lines that are restricted to HLA alleles or HLA allele combinations presenting immunodominant epitopes, clustered by their respective HLA alleles or HLA allele combinations, as described in Example, Section 6.2.3.

5. DETAILED DESCRIPTION

The present invention provides methods of selecting an allogeneic T cell line for therapeutic administration to a human patient having or suspected of having a pathogen or cancer, and methods of selecting an allogeneic T cell donor from whom to derive such an allogeneic T cell line. According to the invention, there is a hierarchy of HLA alleles presenting immunodominant epitopes that leads to preferential expansion of epitope-specific T cells restricted to specific HLA alleles over others inherited and expressed.

The present invention makes use of a representation reflecting this hierarchy of expansion (reflected by anti-pathogen or anti-cancer activity) in order to select allogeneic T cell lines for therapy and to select the donors from whom to derive the allogeneic T cell lines.

There is also a hierarchy of HLA alleles presenting immunodominant epitopes that leads to preferential generation of epitope-specific T cells restricted to specific HLA alleles over others inherited and expressed. The present invention makes use of a representation reflecting this hierarchy of generation (reflected by frequency of generation) in order to select donors from whom to derive T cell lines.

5.1. Selection of T Cell Line for Adoptive Cell Therapy

Provided herein are methods of selecting an allogeneic T cell line for therapeutic administration to a human patient having or suspected of having a pathogen or cancer.

In various aspects, the methods of selecting an allogeneic T cell line for therapeutic administration to a human patient having or suspected of having a pathogen or cancer comprise: selecting a T cell line allogeneic to the patient that recognizes at least one epitope of an antigen of the pathogen or the cancer, using a representation (hereinafter "Representation of Activity") that (i) identifies a plurality of HLA alleles and optionally HLA allele combinations, and (ii) discloses indications of relative activities of T cell lines, each recognizing at least one epitope of an antigen of the pathogen or cancer, and restricted to different ones of the HLA alleles or HLA allele combinations in the plurality; wherein in the representation each identified HLA allele or HLA allele combination is associated with the respective indication of relative activity of the T cell line restricted to the HLA allele or HLA allele combination, the relative activities being relative measures of known activity against the pathogen or against the cancer exhibited by the T cell lines; wherein (A) the T cell line selected has in common with the patient or diseased cells (e.g., of the cancer or associated with the presence of the pathogen) in the patient the HLA allele or HLA allele combination identified by the representation to which the recognition of the T cell line is restricted; and (B) the HLA allele or HLA allele combination, to which the T cell line selected is restricted, is associated in the representation with an indication of the highest relative activity among the HLA alleles and HLA allele combinations in the representation that are known to be in common with the patient or the diseased cells in the patient (based on the HLA assignment of the patient or the diseased cells in the patient) and are not otherwise disqualified. An HLA allele or HLA allele combination is deemed "otherwise disqualified" if the T cell line restricted to that HLA allele or HLA allele combination is known to be unsuitable for therapeutic administration for any reason. For example, if a tentatively selected T cell line is observed to have no or too few viable cells in the cell line sample, the HLA allele or HLA allele combination (to which such T cell line is restricted) can be deemed disqualified. As but another example, if the relative activities in the Representation of Activity are based upon in vitro or ex vivo assays of activity and it is known that the relative in vivo activity of a T cell line restricted to a particular HLA allele or HLA allele combination does not correlate with the relative in vitro or ex vivo assay used for generating the Representation of Activity, such that the highest relative activity in the Representation of Activity is not the highest relative in vivo activity, the particular HLA allele or HLA allele combination (to which such T cell line is restricted) can be deemed disqualified. For example, it has been observed that the in vivo activity against CMV infection in human patients for T cell lines restricted to HLA-B35 is clinically ineffective (therefore negligible relative in vivo activity), although the percentage of interferon-γ-secreting CD3+ T cells derived from T cell lines restricted to HLA-B35 indicates a much higher relative activity; thus, in the context of treating CMV infections, if a T cell line restricted to HLA-B35 is tentatively selected, preferably HLA-B35 would be "otherwise disqualified". By use of the claimed method, the T cell line being selected is specific for an epitope of the pathogen or cancer, presented by a HLA allele or HLA allele combination shared with the patient, that is associated with the highest activity among the HLA alleles or HLA allele combinations in the patient. In a related specific embodiment, an HLA allele or HLA allele combination is deemed disqualified if T cell line(s) restricted to the HLA allele or HLA allele combination are known to be clinically ineffective in treatment of patients having the pathogen or cancer.

In another embodiment, the method provided by the invention is a method of selecting a candidate allogeneic T cell line for therapeutic administration to a human patient having or suspected of having a pathogen or cancer comprising: selecting a T cell line allogeneic to the patient that recognizes at least one epitope of an antigen of the pathogen or the cancer, using a Representation of Activity that (i) identifies a plurality of HLA alleles and optionally HLA allele combinations, and (ii) discloses indications of relative activities of T cell lines, each recognizing at least one epitope of an antigen of the pathogen or cancer, and restricted to different ones of the HLA alleles or HLA allele combinations in the plurality; wherein in the representation each identified HLA allele or HLA allele combination is associated with the respective indication of relative activity of the T cell line restricted to the HLA allele or HLA allele combination, the relative activities being relative measures of known activity against the pathogen or against the cancer exhibited by the T cell lines; wherein (A) the T cell line selected has in common with the patient or diseased cells (e.g., of the cancer or associated with the presence of the pathogen) in the patient the HLA allele or HLA allele combination identified by the representation to which the recognition of the T cell line is restricted; and (B) the HLA allele or HLA allele combination, to which the T cell line selected is restricted, is associated in the representation with an indication of the highest relative activity among the HLA alleles and HLA allele combinations in the representation that are known to be in common with the patient or the diseased cells in the patient (based on the HLA assignment of the patient or the diseased cells in the patient).

In certain embodiments, the methods further comprise prior to the selecting step, a step of generating the Representation of Activity. Methods that can be used for generating the Representation of Activity are described below. In certain embodiments, the methods further comprise prior to the generating step, a step of measuring the relative activities. In certain embodiments, the methods further comprise prior to the selecting step, a step of ascertaining the HLA assignment for the patient or the diseased cells in the patient.

In specific embodiments, the T cell line selected recognizes at least one epitope of an antigen of the pathogen or the cancer, said at least one epitope presented by an HLA allele or HLA allele combination that is in common with the patient or diseased cells in the patient, wherein the HLA allele or HLA allele combination is associated with an indication of the highest relative activity among the HLA alleles and HLA allele combinations in the patient or the diseased cells in the patient (and are not otherwise disqualified as described above). In a preferred aspect of such embodiments, the relative activities are in vivo clinical efficacies of the T cell lines in treatment of patients having the pathogen or cancer.

In specific embodiments of the methods described herein, the at least one epitope is at least one immunodominant epitope.

In certain embodiments of methods of the invention, the T cell line selected has in common with the patient or diseased cells (e.g., of the cancer or associated with the presence of the pathogen) in the patient the HLA allele or HLA allele combination identified by the Representation of Activity to which the recognition of the T cell line is restricted. In some embodiments, the patient is a transplant recipient. In a specific embodiment where the patient is a transplant recipient, the HLA allele(s) or HLA allele combination(s) that are in common with the patient or the diseased cells (e.g., cancerous or infected with a pathogen) in the patient refer to HLA allele(s) or HLA allele combination(s) that are in common with the patient before and/or after the transplant. In some embodiments, the diseased cells in the patient are derived from the transplant given to the patient and thus express the HLA alleles of the transplant; in such an embodiment, determining the HLA assignment of the diseased cells in the patient can be done by typing the HLA alleles in the transplant given to the patient. In other embodiments, the diseased cells in the patient are not derived from the transplant given to the patient, and thus have the HLA assignment of the patient prior to the transplant. In specific embodiments, the transplant is a HSCT or solid organ transplant.

5.1.1. Generation of T Cell Lines

T cell lines from which to select for therapeutic administration and/or to use to obtain information for generation of a representation, can be made as described herein. T cell lines that recognize at least one epitope of an antigen of a pathogen or cancer can be generated by any method known in the art or as described herein. Non-limiting exemplary methods of generating T cell lines that recognize at least one epitope of an antigen of a pathogen or cancer can be found in Trivedi, D., et al., Blood, 2005. 105: 2793-2801; Koehne, G., et al., Blood, 2000. 96: 109-117; Koehne, G., et al., Blood, 2002. 99: 1730-1740; Doubrovina, E., et al., Blood, 2012. 119: 2644-2656; Barker, J. N., et al., Blood, 2010. 116: 5045-5049; O'Reilly, R. J., et al., Immunol Res, 2007. 38: 237-250; and O'Reilly, R. J., et al., Best Practice & Research Clinical Haematology, 2011. 24: 381-391.

In certain embodiments, a T cell line is generated by stimulating T cells from a seropositive donor with antigen presenting cells presenting one or more peptides of antigen (s) displaying the antigenicity of the pathogen or cancer (of the patient). Preferably, the antigen presenting cells are autologous to the T cells (and thus are derived from the donor of the T cells). In specific embodiments, the T cells are stimulated with dendritic cells loaded with a pool of peptides of one or more antigens of the pathogen or cancer. In some embodiments, the dendritic cells are derived from the donor of the T cells. In specific embodiments, the T cells are stimulated with cytokine-activated monocytes (CAMS) loaded with a pool of peptides of one or more antigens of the pathogen or cancer. In some embodiments, the CAMS are derived from the donor of the T cells. In specific embodiments, the T cells are stimulated with peripheral blood mononuclear cells (PBMCs) loaded with a pool of peptides of one or more antigens of the pathogen or cancer. In some embodiments, the PBMCs are derived from the donor of the T cells. In certain embodiments, the T cell lines are generated by stimulating T cells with B lymphocyte cell lines (BLCLs) loaded with a pool of peptides of one or more antigens of the pathogen or cancer. In some embodiments the BLCLs are derived from the donor of the T cells. In specific embodiments, the BLCLs are EBV-transformed BLCLs derived from the donor of the T cells. In certain embodiments, the T cell lines are generated by stimulating T cells with artificial antigen-presenting cells (AAPCs) loaded with a pool of peptides of one or more antigens of the pathogen or cancer.

In various embodiments, the pool of peptides is a pool of overlapping peptides spanning an antigen of the pathogen or cancer. In various embodiments, the pool of peptides is a pool of overlapping peptides spanning more than one antigen of the pathogen or cancer. In a specific embodiment, the pool of overlapping peptides is a pool of overlapping pentadecapeptides.

In certain embodiments, the T cell lines are generated by stimulating T cells with AAPCs genetically engineered to express at least one immunogenic peptide or protein of the pathogen. In certain embodiments, the T cell lines are generated by stimulating T cells with BLCLs that are transformed with a virus, wherein the virus is the pathogen.

In some embodiments, the T cells are stimulated for a period of 28-40 days in culture. In particular embodiments, the T cells are stimulated in the presence of IL-2. In various embodiments, after stimulation the T cell lines are cryopreserved for storage. In a specific embodiment, where a T cell line is selected according to the claimed method that is cryopreserved, the T cell line is thawed before therapeutic administration. In a further specific embodiment, the thawed T cell line optionally is expanded in culture prior to therapeutic administration.

In various embodiments, the T cells that are used for generating the T cell lines are purified by methods known in the art. In certain embodiments, the T cells are enriched from peripheral blood lymphocytes separated from PBMCs. In some embodiments, T cells are enriched from peripheral blood lymphocytes separated from PBMCs by depletion of adherent monocytes followed by depletion of natural killer cells.

Dendritic cells that can be used to stimulate T cells to generate T cell lines recognizing at least one epitope of an antigen of a pathogen or cancer can be derived from cytokine-activated monocytes (CAMS). In some embodiments, the CAMS are generated by incubating PBMCs with cytokines, such as GM-CSF, IL-4, TNF-α, IL-1β, IL-6, and/or prostaglandin-E2.

BLCLs that can be used to stimulate T cells to generate T cell lines recognizing at least one epitope of an antigen of a pathogen or cancer can be generated from PBMCs using any method known in the art, for example, as described in Koehne, G., et al., Blood, 2000. 96: 109-117 or Koehne, G., et al., Blood, 2002. 99: 1730-1740.

The HLA allele or HLA allele combination to which each of the generated T cell lines that recognize at least one epitope of an antigen of a pathogen or cancer is restricted can be determined by any method known in the art, for example, as described in Trivedi, D., et al., Blood, 2005. 105: 2793-2801; Barker, J. N., et al., Blood, 2010. 116: 5045-5049; Hasan, A. N., et al., J Immunol, 2009. 183: 2837-2850; or Doubrovina, E., et al., Blood, 2012. 120: 1633-1646.

5.1.2. Ascertaining the HLA Assignment

The step of ascertaining the HLA assignment (i.e., typing the HLA loci) can be performed by any method known in the art. Non-limiting exemplary methods for ascertaining the HLA assignment can be found in Lange, V., et al., BMC Genomics, 2014. 15: 63; Erlich, H., Tissue Antigens, 2012. 80:1-11; Bontadini, A., Methods, 2012. 56:471-476; Dunn, P. P., Int J Immunogenet, 2011 38:463-473; and Hurley, C. K., "DNA-based typing of HLA for transplantation." in Leffell, M. S., et al., eds., Handbook of Human Immunology, 1997. Boca Raton: CRC Press. In some embodiments, the step of ascertaining the HLA assignment comprises typing at least 4 HLA loci, preferably HLA-A, HLA-B, HLA-C, and HLA-DRB1. In some embodiments, the step of ascertaining the HLA assignment comprises typing 4 HLA loci, preferably HLA-A, HLA-B, HLA-C, and HLA-DRB1. In some embodiments, the step of ascertaining the HLA assignment comprises typing at least 6 HLA loci. In some embodiments, the step of ascertaining the HLA assignment comprises typing 6 HLA loci. In some embodiments, the step of ascertaining the HLA assignment comprises typing at least 8 HLA loci. In some embodiments, the step of ascertaining the HLA assignment comprises typing 8 HLA loci. In some embodiments, the step of ascertaining the HLA assignment comprises typing all of the known HLA loci. In some embodiments, the step of ascertaining the HLA assignment comprises typing less than all of the known HLA loci.

In general, typing more HLA loci is preferable for practicing the invention, since the more HLA loci that are typed, the more likely the allogeneic T cell line selected will have highest activity relative to other allogeneic T cell lines that have HLA alleles or HLA allele combinations in common with the patient or the diseased cells in the patient.

5.1.3. Generation of Representation of Activity for Selecting T Cell Lines

The Representation of Activity identifies a plurality of HLA alleles and optionally HLA allele combinations, and discloses indications of relative activities of T cell lines (i) each recognizing at least one epitope of an antigen of the pathogen or cancer (of the patient), and (ii) restricted to different ones of the HLA alleles or HLA allele combinations in the plurality. In the Representation of Activity, each identified HLA allele or HLA allele combination is associated with the respective indication of relative activity of the T cell line restricted to the HLA allele or HLA allele combination, the relative activities being relative measures of known activity against the pathogen or against the cancer exhibited by the T cell lines.

The relative activities of the T cell lines can be obtained by any in vitro, ex vivo, or in vivo method known in the art.

In preferred embodiments, the relative activities are measured as the in vivo clinical efficacies of the T cell lines in treatment of patients having the pathogen or cancer. In specific aspects of such embodiments, the relative activities can be measured as the percentage of patients having or suspected of having the pathogen or cancer that achieve a complete remission (CR) after treatment with the T cell lines. In specific embodiments, the relative activities are measured as the percentage of patients having or suspected of having the pathogen or cancer that achieve a CR or partial remission (PR) after treatment with the T cell lines.

In some embodiments, the relative activities are measured as the percentage of interferon-γ-producing CD3+ cells derived from each of the T cell lines upon stimulation with antigen presenting cells presenting one or more peptides displaying the antigenicity of the pathogen or cancer. In specific embodiments, wherein the antigen is of CMV or EBV, the relative activities are measured by methods modified from or as described in Koehne, G., et al., Blood, 2002. 99: 1730-1740 or Waldrop, S. L., et al., J Clin Invest, 1997. 99: 1739-1750.

In some embodiments, the relative activities are measured as the percentage of cells expressing an antigen of the pathogen or cancer that are lysed upon exposure to each of the T cell lines in a cytotoxicity assay carried out according to methods known in the art.

According to the present invention, the relative activities are not measured as the binding affinities of the epitope recognized by the respective T cell line to the HLA allele that presents the epitope.

In some aspects, the Representation of Activity is a list of the plurality of HLA alleles and optionally HLA allele combinations ranked by the relative activities. In some embodiments, the step of selecting an allogeneic T cell line is performed by going down the list of the plurality of HLA alleles and optionally HLA allele combinations ranked by the relative activities, with the highest rank in the list being an indication of the highest relative activity, and determining the highest ranked HLA allele or HLA allele combination that is known to be in common with the patient or the diseased cells in the patient, and choosing an allogeneic T cell line restricted to that HLA allele or HLA allele combination. By way of example, in a specific embodiment, the Representation of Activity is a list as shown in Table 6.

In some aspects, the Representation of Activity is a database (e.g., table) listing the plurality of HLA alleles and optionally HLA allele combinations, each associated with a score indicative of relative activity. In some embodiments, the step of selecting an allogeneic T cell line is performed by going through the database listing of the plurality of HLA alleles and optionally HLA allele combinations, each associated with a score indicative of relative activity, with the highest score in the database being an indication of the highest relative activity, and determining the highest scored HLA allele or HLA allele combination that is known to be in common with the patient or the diseased cells in the patient, and choosing an allogeneic T cell line restricted to that HLA allele or HLA allele combination. In a specific embodiment, the step of selecting an allogeneic T cell line using a Representation of Activity, that is such a database, can be carried out by first filtering out (excluding) all the HLA alleles and HLA allele combinations in the database that are not in common with the patient or the diseased cells in the patient, and then determining among those remaining, the HLA allele or HLA allele combination associated with the indication of highest relative activity, and then choosing an allogeneic T cell line restricted to that HLA allele or HLA allele combination.

In some aspects, the Representation of Activity is a scatter plot. In certain embodiments, a first axis of the scatter plot represents different ones of the HLA alleles and optionally HLA allele combinations in the plurality of HLA alleles and optionally HLA allele combinations. In certain embodiments, a second axis of the scatter plot represents relative activities. In a specific embodiment, the second axis of the scatter plot represents percentage of interferon-γ-secreting $CD3^+$ cells derived from each T cell line for which an indication of relative activity is disclosed in the Representation of Activity, upon stimulation with antigen presenting cells presenting one or more peptides of one or more antigens displaying the antigenicity of the pathogen or cancer. In a particular embodiment, the stimulation is with antigen presenting cells that are autologous to the respective T cell line and are loaded with one or more peptides displaying the antigenicity of the pathogen or cancer, as the indication of said relative activity. By way of example, in a specific embodiment, the Representation of Activity is a scatter plot as shown in FIG. 1.

In some embodiments, the Representation of Activity is stored in a database.

In various embodiments, the method of selecting an allogeneic T cell line is computer-implemented. In some embodiments, the method of selecting an allogeneic T cell line is computer-implemented using a computer system as described in Section 5.6. In some embodiments, the methods of selecting an allogeneic T cell line is computer-implemented using a computer readable medium as described in Section 5.6.

Additional data can be used to update a Representation of Activity once the additional data is available.

5.2. Therapeutic Uses of Selected T Cell Lines

Also provided herein are methods of treating a human patient having or suspected of having a pathogen or cancer, comprising: (a) selecting an allogeneic T cell line for therapeutic administration to the patient according to any of the methods of selecting an allogeneic T cell line as described in Section 5.1; and (b) administering a population of T cells derived from the selected allogeneic T cell line to the patient. Thus, in a patient having a cancer, the invention provides a method of treating the cancer; in a patient having a pathogen, the invention provides a method of treating a disease, disorder, or condition associated with the presence of the pathogen.

In certain embodiments, the administering is by infusion of a population of T cells derived from the selected allogeneic T cell line. In some embodiments, the administering is by bolus intravenous infusion of a population of T cells derived from the selected allogeneic T cell line. The amount to be administered can be determined based on the condition of the patient and the knowledge of the physician. In certain embodiments, the administering comprises administering at least about $1\times10^5$ T cells/kg/dose/week to the patient, wherein the population of T cells is derived from the selected allogeneic T cell line. In some embodiments, the administering comprises administering about $1\times10^6$ to $2\times10^6$ T cells/kg/dose/week to the patient, wherein the population of T cells is derived from the selected allogeneic T cell line. In some embodiments, the administering comprises administering about $1\times10^6$ cells/kg/dose/week to the patient, wherein the population of T cells is derived from the selected allogeneic T cell line. In some embodiments, the administering comprises administering about $2\times10^6$ T cells/kg/dose/week to the patient, wherein the population of T cells is derived from the selected allogeneic T cell line. In certain embodiments, the above-described dosage regimens are carried out for at least 3 weeks, such that at least 3 doses are administered. In some embodiments, the above-described dosage regimens are carried out for 3 weeks, such that 3 doses are administered. In some embodiments, the above-described dosage regimens are carried out for 6 weeks, such that 6 doses are administered. In certain embodiments, the above-described dosage regimens are carried out for 3 weeks, such that 3 doses are administered, followed by administering a population of T cells derived from the selected allogeneic T cell line by another dosage regimen for at least one week, wherein the second dosage regimen is about $1\times10^7$ T cells/kg/dose/week. In certain embodiments, the above-described dosage regimens are carried out for 3 weeks, such that 3 doses are administered, followed by administering a population of T cells derived from the selected allogeneic T cell line by another dosage regimen for three weeks, wherein the second dosage regimen is about $1\times10^7$ T cells/kg/dose/week. In certain embodiments, wherein the patient has a cancer, 5 repeated infusions of doses of about $1\times10^8$ to $1\times10^9$ T cells/kg/dose/week are administered.

5.3. Selection of T Cell Donor for Adoptive Cell Therapy

Also provided herein are methods of selecting an allogeneic T cell donor from whom to derive an allogeneic T cell line for therapeutic administration to a human patient having or suspected of having a pathogen or cancer.

5.3.1. Selection of T Cell Donor Based on Representation of Activity

In various aspects, the methods of selecting an allogeneic T cell donor from whom to derive an allogeneic T cell line for therapeutic administration to a human patient having or suspected of having a pathogen or cancer comprise: selecting a T cell donor allogeneic to the patient, using a Representation of Activity that (i) identifies a plurality of HLA alleles and optionally HLA allele combinations, and (ii) discloses indications of relative activities of T cell lines, each recognizing at least one epitope of an antigen of the pathogen or cancer, and restricted to different ones of the HLA alleles or HLA allele combinations in the plurality; wherein in the representation each identified HLA allele or HLA allele combination is associated with the respective indication of relative activity of the T cell line restricted to the HLA allele or HLA allele combination, the relative activities being relative measures of known activity against the pathogen or against the cancer exhibited by the T cell lines; wherein (A) the T cell donor selected has at least one HLA allele or HLA allele combination in common with the patient or diseased cells (e.g., of the cancer or associated with the presence of the pathogen) in the patient; and (B) one of the at least one HLA allele or HLA allele combination in common with the patient or the diseased cells in the patient is associated in the representation with an indication of the highest relative activity among the HLA alleles and HLA allele combinations in the Representation of Activity that are known to be in common with the patient or the diseased cells in the patient and are not otherwise disqualified. An HLA allele or HLA allele combination is deemed "otherwise disqualified" if the T cell line restricted to that HLA allele or HLA allele combination is known to be unsuitable for therapeutic administration for any reason. For example, if the relative activities in the Representation of Activity are based upon in vitro or ex vivo assays of activity and it is known that the relative in vivo activity of a T cell line restricted to a particular HLA allele or HLA allele combination does not correlate with the relative in vitro or ex vivo assay used for generating the Representation of Activity, such that the highest relative activity in the Representation of Activity is not the highest relative in vivo activity, the particular HLA allele or HLA allele combination (to which such T cell line is restricted) can be deemed disqualified. For example, it has been observed that the in vivo activity against CMV infection in human patients for T cell lines restricted to HLA-B35 is clinically ineffective (therefore negligible relative in vivo activity), although the percentage of interferon-γ-secreting CD3+ T cells derived from T cell lines restricted to HLA-B35 indicates a much higher relative activity; thus, in the context of treating CMV infections, if a T cell donor having HLA-B35 is tentatively selected, preferably HLA-B35 would be "otherwise disqualified". In a related specific embodiment, the HLA allele or HLA allele combination will be deemed disqualified if T cell line(s) restricted to the HLA allele or HLA allele combination are known to be clinically ineffective in treatment of patients having the pathogen or cancer.

In another embodiment, the method provided by the invention is a method of selecting a candidate allogeneic T cell donor from whom to derive an allogeneic T cell line for therapeutic administration to a human patient having or suspected of having a pathogen or cancer comprising: selecting a T cell donor allogeneic to the patient, using a Representation of Activity that (i) identifies a plurality of HLA alleles and optionally HLA allele combinations, and (ii) discloses indications of relative activities of T cell lines, each recognizing at least one epitope of an antigen of the pathogen or cancer, and restricted to different ones of the HLA alleles or HLA allele combinations in the plurality; wherein in the representation each identified HLA allele or HLA allele combination is associated with the respective indication of relative activity of the T cell line restricted to the HLA allele or HLA allele combination, the relative activities being relative measures of known activity against the pathogen or against the cancer exhibited by the T cell lines; wherein (A) the T cell donor selected has at least one HLA allele or HLA allele combination in common with the patient or diseased cells (e.g., of the cancer or associated with the presence of the pathogen) in the patient; and (B) one of the at least one HLA allele or HLA allele combination in common with the patient or the diseased cells in the patient is associated in the representation with an indication of the highest relative activity among the HLA alleles and HLA allele combinations in the Representation of Activity that are known to be in common with the patient or the diseased cells in the patient.

In certain embodiments, the methods further comprise prior to the selecting step, a step of generating the Representation of Activity. Methods that can be used for generating the Representation of Activity are described in Section 5.1.3. In certain embodiments, the methods further comprise prior to the generating step, a step of measuring the relative activities. In certain embodiments, the methods further comprise prior to the selecting step, a step of ascertaining the HLA assignment of the patient or the diseased cells in the patient. In certain embodiments, the methods further comprise prior to the selecting step, a step of ascertaining the HLA assignment for the T cell donor. In certain embodiments, the methods further comprise prior to the selecting step, a step of ascertaining the HLA assignment of the patient or the diseased cells in the patient and the HLA assignment for the T cell donor.

In specific embodiments, the T cell donor selected has at least one HLA allele or HLA allele combination that is in common with the patient or the diseased cells in the patient, wherein one of the at least one HLA allele or HLA allele combination is associated with an indication of the highest relative activity among the HLA alleles and HLA allele combinations in the patient (and are not otherwise disqualified as described above). In a preferred aspect of such embodiments, the relative activities are in vivo clinical efficacies of the T cell lines in treatment of patients having the pathogen or cancer.

In specific embodiments of the methods described herein, the at least one epitope is at least one immunodominant epitope.

In certain embodiments of methods of the invention, the T cell donor selected has at least one HLA allele or HLA allele combination in common with the patient or diseased cells (e.g., of the cancer or associated with the presence of the pathogen) in the patient. In some embodiments, the patient is a transplant recipient. In a specific embodiment where the patient is a transplant recipient, the HLA allele(s) or HLA allele combination(s) that are in common with the patient or the diseased cells (e.g., cancerous or infected with a pathogen) in the patient refer to HLA allele(s) or HLA allele combination(s) that are in common with the patient before and/or after the transplant. In some embodiments, the diseased cells in the patient are derived from the transplant given to the patient and thus express the HLA alleles of the transplant; in such an embodiment, determining the HLA assignment of the diseased cells in the patient can be done by typing the HLA alleles in the transplant given to the patient. In other embodiments, the diseased cells in the patient are not derived from the transplant given to the patient, and thus have the HLA assignment of the patient prior to the transplant. In specific embodiments, the transplant is a HSCT or solid organ transplant.

T cell lines for generation of a Representation of Activity can be made as described in Section 5.1.1.

The step of ascertaining the HLA assignment can be performed as described in Section 5.1.2. In general, typing more HLA loci is preferable for practicing the invention, since the more HLA loci that are typed, the more likely the T cell donor selected will derive an allogeneic T cell line having the highest activity relative to other allogeneic T cell lines derived from other T cell donors who have at least one HLA allele or HLA allele combination in common with the patient or the diseased cells in the patient.

5.3.1.1. Generation of Representation of Activity for Selecting Donors

Representation of Activity can be the same as discussed in Section 5.1.3, and made as described therein.

In some aspects, the Representation of Activity is a list of the plurality of HLA alleles and optionally HLA allele combinations ranked by the relative activities. In some embodiments, the step of selecting of an allogeneic T cell donor is performed by going down the list of the plurality of HLA alleles and optionally HLA allele combinations ranked by the relative activities, with the highest rank in the list being an indication of the highest relative activity, and determining the highest ranked HLA allele or HLA allele combination that is known to be in common with the patient or the diseased cells in the patient, and choosing an allogeneic T cell donor who has that HLA allele or HLA allele combination. By way of example, in a specific embodiment, the Representation of Activity is a list as shown in Table 6.

In some aspects, the Representation of Activity is a database (e.g., table) listing the plurality of HLA alleles and optionally HLA allele combinations, each associated with a score indicative of relative activity. In some embodiments, the step of selecting an allogeneic T cell donor is performed by going through the database listing of the plurality of HLA alleles and optionally HLA allele combinations, each associated with a score indicative of relative activity, with the highest score in the database being an indication of the highest relative activity, and determining the highest scored HLA allele or HLA allele combination that is known to be in common with the patient or the diseased cells in the patient, and choosing an allogeneic T cell donor who has that HLA allele or HLA allele combination. In a specific embodiment, the step of selecting an allogeneic T cell donor using a Representation of Activity, that is such a database, can be carried out by first filtering out (excluding) all the HLA alleles and HLA allele combinations in the database that are not in common with the patient or the diseased cells in the patient, and then determining among those remaining, the HLA allele or HLA allele combination associated with the indication of highest relative activity, and then choosing an allogeneic T cell donor who has that HLA allele or HLA allele combination.

In some aspects, the Representation of Activity is a scatter plot. In certain embodiments, a first axis of the scatter plot represents different ones of the HLA alleles and optionally HLA allele combinations in the plurality of HLA alleles and optionally HLA allele combinations. In certain embodiments, a second axis of the scatter plot represents relative activities. In a specific embodiment, the second axis of the scatter plot represents percentage of interferon-γ-secreting $CD3^+$ cells derived from each T cell line for which an indication of relative activity is disclosed in the Representation of Activity, upon stimulation with antigen presenting cells presenting one or more peptides of one or more antigens displaying the antigenicity of the pathogen or cancer. In a particular embodiment, the stimulation is with antigen presenting cells that are autologous to the respective T cell line and are loaded with one or more peptides displaying the antigenicity of the pathogen or cancer, as the indication of said relative activity. By way of example, in specific embodiments, the representation of activity is a scatter plot as shown in FIG. 1.

In some embodiments, the Representation of Activity is stored in a database.

In various embodiments, the method of selecting an allogeneic T cell donor as described herein is computer-implemented. In some embodiments, the method of selecting an allogeneic T cell donor as described herein is computer-implemented using a computer system as described in Section 5.6. In some embodiments, the methods of selecting an allogeneic T cell donor as described in Section 5.3.1 is computer-implemented using a computer readable medium as described in Section 5.6.

Additional data can be used to generate a Representation of Activity once the additional data is available.

5.3.2. Selection of T Cell Donor Based on Representation of Frequency

In various aspects, the methods of selecting an allogeneic T cell donor from whom to derive an allogeneic T cell line for therapeutic administration to a human patient having or suspected of having a pathogen or cancer comprise: selecting a T cell donor allogeneic to the patient who has in common one or more HLA alleles with the patient or diseased cells (e.g., of the cancer or associated with the presence of the pathogen) in the patient t, using a representation (hereinafter "Representation of Frequency") that (i) identifies a plurality of HLA alleles, and (ii) discloses indications of relative frequencies of generation of T cell lines, each recognizing at least one epitope of an antigen of the pathogen or the cancer, and restricted to different ones of said HLA alleles in the plurality; wherein in the representation each identified HLA allele is associated with the respective indication of relative frequency of generation of said T cell lines restricted to the HLA allele, wherein: the T cell donorselected has at least one HLA allele in common with the patient or the diseased cells in the patient that is associated in the representation with an indication of higher frequency of generation than HLA alleles of the donor that are not in common with the patient or the diseased cells in the patient.

In another embodiment, the method provided by the invention is a method of selecting a candidate allogeneic T cell donor from whom to derive an allogeneic T cell line for therapeutic administration to a human patient having or suspected of having a pathogen or cancer comprising: selecting a T cell donor allogeneic to the patient who has in common one or more HLA alleles with the patient or diseased cells (e.g., of the cancer or associated with the presence of the pathogen) in the patient t, using a Representation of Frequency that (i) identifies a plurality of HLA alleles, and (ii) discloses indications of relative frequencies of generation of T cell lines, each recognizing at least one epitope of an antigen of the pathogen or the cancer, and restricted to different ones of said HLA alleles in the plurality; wherein in the representation each identified HLA allele is associated with the respective indication of relative frequency of generation of said T cell lines restricted to the HLA allele, wherein: the T cell donorselected has at least one HLA allele in common with the patient or the diseased cells in the patient that is associated in the representation with an indication of higher frequency of generation than HLA alleles of the donor that are not in common with the patient or the diseased cells in the patient.

In certain embodiments, the methods further comprise prior to the selecting step, a step of generating the Representation of Frequency. Methods that can be used for generating the Representation of Frequency are described below. In certain embodiments, the methods further comprise prior to the generating step, a step of measuring the relative frequencies. In certain embodiments, the methods further comprise prior to the selecting step, a step of ascertaining the HLA assignment for the patient or the diseased cells in the patient. In certain embodiments, the methods further comprise prior to the selecting step, a step of ascertaining the HLA assignment for the T cell donor. In certain embodiments, the methods further comprise prior to the selecting step, a step of ascertaining the HLA assignment for the patient or the diseased cells in the patient and the HLA assignment for the T cell donor.

In specific embodiments of the methods described herein, the at least one epitope is at least one immunodominant epitope.

In certain embodiments of methods of the invention, the T cell donor selected has at least one HLA allele in common with the patient or diseased cells (e.g., of the cancer or associated with the presence of the pathogen) in the patient that is associated in the Representation of Frequency with an indication of higher frequency of generation than HLA alleles of the donor that are not in common with the patient or the diseased cells in the patient. In some embodiments, the patient is a transplant recipient. In a specific embodiment where the patient is a transplant recipient, the HLA allele(s) that are in common with the patient or the diseased cells (e.g., cancerous or infected with a pathogen) in the patient refer to HLA allele(s) that are in common with the patient before and/or after the transplant. In some embodiments, the diseased cells in the patient are derived from the transplant given to the patient and thus express the HLA alleles of the transplant; in such an embodiment, determining the HLA assignment of the diseased cells in the patient can be done by typing the HLA alleles in the transplant given to the patient. In other embodiments, the diseased cells in the patient are not derived from the transplant given to the patient, and thus have the HLA assignment of the patient prior to the transplant. In specific embodiments, the transplant is a HSCT or solid organ transplant.

T cell lines for generation of a Representation of Frequency can be made as described in Section 5.1.1.

The step of ascertaining the HLA assignment can be performed as described in Section 5.1.2. In general, typing more HLA loci is preferable for practicing the invention.

The step of ascertaining the HLA assignment can be performed as described in Section 5.1.2.

5.3.2.1. Generation of Representation of Frequency for Selecting Donors

The Representation of Frequency identifies a plurality of HLA alleles, and discloses indications of relative frequencies of generation of T cell lines (i) each recognizing at least one epitope of an antigen of the pathogen or the cancer (of the patient), and (ii) restricted to different ones of the HLA alleles. In the Representation of Frequency, each identified HLA allele is associated with the respective indication of relative frequency of generation of the T cell lines restricted to the HLA alleles.

In some aspects, the Representation of Frequency is a list of the plurality of HLA alleles ranked by the relative frequencies. In some embodiments, the step of selecting an allogeneic T cell donor is performed by going down the list of the plurality of HLA alleles ranked by the relative frequencies, with the highest rank in the list being an indication of the highest relative frequency, and choosing an allogeneic T cell donor who has at least one HLA allele in common with the patient or the diseased cells in the patient that is associated in the list with a higher rank than HLA alleles of the donor that are not in common with the patient or the diseased cells in the patient.

In some aspects, the Representation of Frequency is a database (e.g., table) listing the plurality of HLA alleles, each associated with a score indicative of relative frequency. In some embodiments, the step of selecting an allogeneic T cell donor is performed by going through the database listing the HLA alleles, each associated with a score indicative of relative frequency, with the highest score in the database being an indication of the highest relative frequency, and choosing an allogeneic T cell donor who has at least one HLA allele in common with the patient or the diseased cells in the patient that is associated in the database with a higher score than HLA alleles of the donor that are not in common with the patient or the diseased cells in the patient.

In some embodiments, the Representation of Frequency is stored in a database.

In various embodiments, the method of selecting an allogeneic T cell donor as described in this disclosure is computer-implemented. In some embodiments, the method of selecting an allogeneic T cell donor as described in this disclosure is computer-implemented using a computer system as described in Section 5.6. In some embodiments, the methods of selecting an allogeneic T cell donor as described in this disclosure is computer-implemented using a computer readable medium as described in Section 5.6.

Additional data can be used to update a Representation of Frequency once the additional data is available.

5.4. Obtaining T Cell Line

Also described herein are methods of obtaining an allogeneic T cell line for therapeutic administration to a human patient having or suspected of having a pathogen or cancer, comprising: (a) selecting an allogeneic T cell donor according to a method as described in Section 5.3; and (b) deriving an allogeneic T cell line from the selected allogeneic T cell donor, which allogeneic T cell line recognizes at least one epitope of an antigen or the pathogen or cancer.

5.5. Patients

The patient referred to in this disclosure is a human patient.

In various embodiments, the patient has been the recipient of a transplant. In a specific embodiment, the transplant is a HSCT. In certain embodiments, the HSCT is a bone marrow transplant (BMT). In certain embodiments, the HSCT is a peripheral blood stem cell transplant (PBSCT). In certain embodiments, the HSCT is a cord blood transplant (CBT). In a specific embodiment, the transplant is a solid organ transplant.

In various embodiments, the patient has not been the recipient of a transplant. In a specific embodiment, the patient has not been a recipient of HSCT. In a specific embodiment, the patient has not been a recipient of solid organ transplant.

In various aspects, the patient has or is suspected of having a pathogen. In a specific embodiment, the patient has the pathogen. In a specific embodiment, the patient is seropositive for the pathogen, and has symptoms of an infection by the pathogen. The pathogen can be a virus, bacterium, fungus, helminth, or protist. In certain embodiments, the pathogen is a virus.

In some embodiments, the virus is cytomegalovirus (CMV). In specific embodiments, the patient has or is suspected of having a CMV infection subsequent to the patient having undergone a HSCT. In particular embodiments, the antigen of CMV is CMV pp65. In particular embodiments, the antigen of CMV is CMV IE1.

In some embodiments, the virus is Epstein-Barr virus (EBV). In particular embodiments, the antigen of EBV is EBNA1, EBNA2, EBNA3A, EBNA3B, EBNA3C, LMP1, or LMP2.

In some embodiments, the virus is polyoma BK virus (BKV), John Cunningham virus (JCV), herpesvirus, adenovirus (ADV), human immunodeficiency virus (HIV), influenza virus, ebola virus, poxvirus, rhabdovirus, or paramyxovirus. In particular embodiments, the virus is BKV. In particular embodiments, the virus is JCV. In particular embodiments, the virus is ADV. In particular embodiments, the virus is human herpesvirus-6 (HHV-6) or human herpesvirus-8 (HHV-8).

In one embodiment, the patient has a viral infection that is not responsive to antiviral (small molecule) drug therapy.

In various aspects, the patient has or is suspected of having a cancer. In a specific embodiment, the patient has a cancer. The cancer can include a cancer of the blood, breast, lung, ovary, stomach, pancreas, larynx, esophagus, testes, liver, parotid, biliary tract, colon, rectum, cervix, uterus, endometrium, kidney, bladder, prostate, thyroid, brain or skin. In some embodiments, the cancer is a cancer of the blood. In specific embodiments, the cancer is a lymphoproliferative disorder. In other embodiments, the cancer is a cancer of the brain.

In some embodiments, the cancer is WT1-positive cancer. In specific embodiments, the antigen of the cancer is WT1.

In some embodiments, the cancer is EBV-positive post-transplant lymphoproliferative disorder (EBV-PTLD). In specific embodiments, the antigen of an EBV-PTLD is EBNA1, EBNA2, EBNA3A, EBNA3B, or EBNA3C. In further specific embodiments, the antigen is LMP1 or LMP2.

In some embodiments, the cancer is EBV-positive nasopharyngeal carcinoma. In specific embodiments, the antigen of the EBV-positive nasopharyngeal carcinoma is EBNA1, LMP1, or LMP2.

An antigen of a cancer, as described herein, can be a cancer-specific or cancer-associated antigen, and thus can be a peptide or protein whose expression is higher in the cancer tissue or cancer cells than in non-cancerous tissues or non-cancerous cells, or a peptide or protein which is uniquely expressed in the cancer tissue or cancer cells relative to non-cancerous tissues or non-cancerous cells.

5.6. Computer Systems and Computer Readable Media

In various embodiments, a computer system or computer readable medium is configured for carrying out any of the methods of selecting an allogeneic T cell line, and any of the methods of selecting an allogeneic T cell donor as described in this disclosure.

Also provided herein are computer systems for selecting an allogeneic T cell line for therapeutic administration to a human patient having or suspected of having a pathogen or cancer. In a specific embodiment such a computer system comprises: a central processing unit; a memory, coupled to the central processing unit, the memory storing instructions for performing the step(s) of any of the methods of selecting an allogeneic T cell line or any of the methods of selecting an allogeneic T cell donor as described in this disclosure. In some embodiments, the computer system further comprises a display device in operable communication with the central processing unit.

Also provided herein are computer readable media having computer-executable instructions for performing the step(s) of any of the methods of selecting an allogeneic T cell line or any of the methods of selecting an allogeneic T cell donor as described in this disclosure.

In some embodiments, loaded into a computer system or computer readable medium are software components that are standard in the art. The software components collectively cause the computer system to function according to a method of selecting an allogeneic T cell lines or the methods of selecting an allogeneic T cell donor as described in this disclosure. In some embodiments, loaded into the computer system or computer readable medium are software components that are standard in the art, and one or more computer program products that are special to the instant invention. In specific embodiments, the one or more computer program products cause a computer system to function according to a method of selecting an allogeneic T cell lines or the methods of selecting an allogeneic T cell donor as described in this disclosure. In specific embodiments, the one or more computer program products that are special to the instant invention and the software components that are standard in the art collectively cause the computer system to function according to a method of selecting an allogeneic T cell lines or the methods of selecting an allogeneic T cell donor as described herein.

In certain embodiments, the computer system or computer readable medium is configured to select an allogeneic T cell line for therapeutic administration to the patient for high and consistent efficacy. In certain embodiments, the computer system or computer readable medium is configured to select an allogeneic T cell donor from whom to derive an allogeneic T cell line for therapeutic administration to the patient for high and consistent efficacy.

6. EXAMPLE

Certain embodiments provided herein are illustrated by the following non-limiting example, which demonstrates a technology permitting optimized selection of therapeutically active CMVpp65-specific T-cells from banked HLA partially matched third party donor-derived T-cell lines for treatment of CMV infections based on the hierarchy of HLA alleles shared by donor and recipient that present immunodominant viral peptides.

6.1. Methods:

6.1.1. Establishment of CMV CTL Bank:

All cellular products were processed in the GMP facility at Memorial Sloan Kettering Cancer Center (MSKCC) under standard operating procedures (SOPs) and FDA compliant protocols.

6.1.1.1. Generation of Autologous Cytokine-Activated Monocytes (CAMS):

Peripheral blood mononuclear cells (PBMC) were isolated from the blood of seropositive donors by density gradient centrifugation using ficoll hypaque.

PBMC at a concentration of $10^7$/ml suspended in RPM-1640 with 1% autologous serum were allowed to adhere in 6 well tissue culture plates at 37° C. for 2 hours following which the non-adherent mononuclear cells were gently removed. The adherent monocytes cultured with 2 ml serum free IMDM per well and supplemented with GM-CSF 2000 IU (50 µl) and IL-4 1000 U (25 µl) of IL-4 every other day until day 5. On day 5, tumor necrosis factor-α (SIGMA, St. Louis) was added to achieve a final concentration of 10 ng/ml, Interleukin-1β to 400 IU/ml, interleukin-6 (R&D systems, Inc, Minneapolis, Minn. USA) to 1000 IU/ml and prostaglandin-E2 (Calbiochem, La Jolla, Calif. USA) to 25 mm/ml to induce final maturation of the CAMS. On day 7 the mature CAMS were harvested, characterized as to their expression of HLA Class II, CD14 and co-stimulatory molecules by FACS counted, aliquoted and used for sensitization of T-cell lines as detailed below.

6.1.1.2. Generation of Autologous Transformed B Lymphocyte Cell Lines (BLCL):

EBV-BLCLs from each donor were generated by infections of PBMC with EBV strain B95.8 as previously described (Koehne, G., et al., Blood, 2000. 96: 109-117; Koehne, G., et al., Blood, 2002. 99: 1730-1740). The cells were maintained in RPMI 1640 (Invitrogen, Inc, Carlsbad, Calif. USA) supplemented with 10% fetal calf serum (FCS), and acyclovir.

6.1.1.3. Generation of CMVpp65 Specific T-Cells:

T-cells were enriched from peripheral blood lymphocytes separated from the PBMCs by depletion of adherent monocytes followed by depletion of natural killer cells by using immunomagnetic separation of CD56+ cells with immunomagnetic CD56 precoated microbeads (Miltenyi Biotech Inc.). Purified T-cells were then co-cultured with irradiated autologous CAMS loaded with a GMP grade pool of overlapping pentadecapeptides (PL CAMs) as previously described (Trivedi, D., et al., Blood, 2005. 105: 2793-2801). T-cells were cultured for a period of 28-40 days in the presence of IL-2 (5-40 U/ml), and re-stimulated weekly with irradiated autologous peptide-loaded CAMS, at an effector to stimulator ratio of 20:1 as previously described (Trivedi, D., et al., Blood, 2005. 105: 2793-2801).

6.1.2. Characterization of CMVpp65 Specific T-Cells:

6.1.2.1. Tetramer Analysis:

The proportion of CMVpp65 epitope specific T-cells were quantitated using HLA-peptide tetramers using commercially available CMVpp65 MHC-peptide tetramers for HLA A0201, A2402 and B0702 bearing peptide sequences NLVPMVATV, QYDPVAALF and TPRVTGGGAM respectively (Beckman Coulter, Inc Fullerton, Calif.). T-cells were incubated with CD3 FITC, CD8 PE, CD4 PerCP (BD Bioscience, San Jose, Calif.) and APC conjugated tetrameric complex for 20 minutes on ice, washed and subsequently analyzed by FACS (BD LSR II). Data were analyzed using Flowjo software (Tree Star Inc, Ashland, Oreg.). The proportion of CD4 and CD8+ T-cells within the cultures, as well as the proportion of CD3+, and CD8+ T-cells binding to the HLA-peptide tetramers was determined.

6.1.2.2. TCR Vβ Repertoire

CMV peptide-HLA tetramer+ T-cells were analyzed for TCRVβ repertoire via flow cytometry using commercially available kit containing antibodies to 24 subfamilies of the Vβ region of the human TCR (TO Test® Beta Mark, Beckman Coulter, Inc, France) according to procedures provided by the manufacturer (Wei, S., et al., Immunogenetics, 1994. 40: 27-36).

6.1.2.3. Quantitation of CMV-Specific and Alloreactive IFN-γ-Producing T Cells At the onset and at several points in the development of each CMV-specific T-cell line, donor T lymphocytes at a concentration of $1 \times 10^6$/mL were mixed with autologous CAMS that were loaded with the pool of CMVpp65 peptides (20 ug/ml) at an effector-stimulator cell ratio of 5:1. Control tubes containing effector cells and PBMCs not loaded with any peptide were set up in parallel. Brefeldin A was added to nonstimulated and peptide stimulated samples at a concentration of 10 μg/mL cells. Tubes were incubated overnight for 16 hours in a humidified 5% $CO_2$ incubator at 37° C.

Aliquots of the bulk nonstimulated and of the stimulated cultures were transferred to tubes for staining with monoclonal antibodies. Cells were stained with 5 μL monoclonal anti-CD3 labeled with allophycocyanin (APC) and 10 μL anti-CD8 peridin chlorophyll protein (PerCP) or anti-CD4 PerCP (BD Biosciences, San Jose, Calif.) and were incubated for 20 minutes at room temperature in the dark. Cells were washed with 2 mL phosphate-buffered saline (PBS)-bovine serum albumin (BSA)-azide (AZ) (PBS+0.5% BSA+ 0.1% AZ). Cells were centrifuged, supernatant discarded, and 100 μL reagent A (Fix & Perm Cell Permeabilization Reagents A & B; Caltag Laboratories, Burlingame, Calif.) was added to each tube to fix the cells. These cells were then incubated for 15 minutes. Cells were washed with PBS+ BSA+AZ, and 100 μL reagent B (Caltag Laboratories) was added for permeabilization. Intracellular staining was performed by adding 10 μL mouse IgG1 isotype control fluorescein isothiocyanate (FITC) or IFN-γ FITC (BD PharMingen, San Diego, Calif.) monoclonal antibody. Cells were incubated for 20 minutes at room temperature, in the dark, washed twice, and further fixed in 1% formalin.

Stained and fixed cells were subsequently acquired using an LSR II flow cytometer with three lasers for 10-color capability (BD Biosciences), and analyzed using flowjo software. Cells were first identified by forward and side light scatter and then by gating the CD3+ cells in a CD3 APC versus side scatter dot plot. Twenty to Fifty thousand events were acquired in the combined gate. For further identification of the cells, gating on the CD3+CD8+ or CD3+CD4+ cells was performed. Quadrant markers were established based on analysis of the nonstimulated control and isotype control tubes.

6.1.3. Establishing the Hierarchy: Quantitating Antiviral CD8+ T-Cell Responses to Different CMVpp65 Epitopes

6.1.3.1. Epitope Mapping Using a Library of Overlapping 15 aa Peptides

T-cell responses to specific peptides within CMV pp65 were identified and quantitated by measuring the number of IFNγ positive T-cells generated upon secondary stimulation with autologous APCs loaded with the peptides or peptide pool (PL) of interest, according to the technique of Waldrop et al (Waldrop, S. L., et al., J Clin Invest, 1997. 99: 1739-1750) as modified by Koehne et al (Koehne, G., et al., Blood, 2002. 99: 1730-1740). A grid of overlapping peptide pools permitted the identification of specific epitopes inducing T-cell responses. Peptide-loaded PBMCs that were autologous to the T cell donor, CAMS that were autologous to the T cell donor, or BLCL that was autologous to the T cell donor was used as APC to stimulate the responding T-cells for epitope mapping.

6.1.3.2. In-Vitro Cytotoxic Activity

All T-cells lines were assessed for their capacity to lyse CMVpp65 loaded targets using a standard $^{51}$chromium release assay as previously described (Koehne, G., et al., Blood, 2002. 99: 1730-1740; Trivedi, D., et al., Blood, 2005. 105: 2793-2801). Targets used in all experiments consisted of a panel of EBV-BLCL, each sharing with T-cells of a given donor a single HLA allele. These cells were loaded, as specified for a given experiment, with the complete pool of CMVpp65 peptides, or specific sub-pools thereof, single pentadecapeptides, or a CMV pp65 nonamer known to be presented by that allele (e.g. NLVPMVATV for HLA A0201, QYDPVAALF for HLA A2402 and TPRVTGGGAM and RPHERNGFTV for HLA B0702) (Trivedi, D., et al., Blood, 2005. 105: 2793-2801; Hasan, A. N., et al., J Immunol, 2009. 183: 2837-2850). Targets loaded with peptides not presented by the shared HLA allele were used as controls. HLA restriction was identified by reactivity against targets pulsed with an identified peptide epitope presented on a specific shared HLA allele, and absence of reactivity against peptide loaded on either EBV BLCL bearing other shared alleles or fully mismatched EBV BLCL.

6.2. Data:

6.2.1. GMP Grade CMV CTL Bank Generated from a Genotypically Heterogeneous Donor Population Inheriting a Diverse Array of HLA Alleles A total of 119 CMVpp65 specific CTL lines have been generated over a span of 7 years since the initiation of the clinical trial using donor derived CMVpp65 specific T-cells for treatment of CMV viremia in recipients of allogeneic HSCT.

The pool of donors used for the generation of the CTL lines inherited 180 different HLA alleles which were representative of the common HLA alleles prevalent in the multiethnic population of New York. The distribution of the HLA alleles in the donor CTL pool also closely correlated with the HLA allele frequencies represented in each of the ethnic populations including Caucasian, Asian and blacks, except for HLA A0201 and B0702, which were over represented; 33% vs 25% and 21% vs 8.7% respectively (Table 1). The order of the frequency of inherited HLA class-I alleles among the 119 donors was as follows: A0201 (n=39), A0301 (n=28), B0702 (n=25), B 44 (n=24), HLA B 0801 (n=22), B 3501-11 (n=19), A1101 (n=16), A2402 (n=14), B 1501-17 (n=14), B 1801-07 (n=12), A 3201-03 (n=11), A3301-04 (n=10), B 4001-06 (n=9), and A2601 (n=9), B 5701 (n=9). Other HLA class-I alleles were represented at lower frequencies, such as HLA B 5201 (n=8), B 3801 (n=6), A6801-09 (n=5), B 5801 (n=5). For HLA class-II alleles, there were 6 HLA DRB1 alleles that were highly represented, as expected from their higher frequencies in the general population (Table 1.). In order of frequency, these included DRB1 1501-08, 0401-32, 0301-13, 0701-04, 1101-20, 1301-34.

TABLE 1

HLA allele frequencies in general population and characterization of 119 CMVpp65 specific CTL lines.

| | | | | CTL Lines = 119 | | |
|---|---|---|---|---|---|---|
| | HLA Allele Frequency in General Population | | | CTL Lines Inheriting Allele | HLA Allele Restricting T cell Cytotoxic Response | |
| HLA Allele | Cauc. | Black | Oriental | | N | % CTL Lines |
| A0101 | 14.07 | 4.85 | 3.66 | 23 | 3 | 12 |
| A0201 | 25.01 | 15.75 | 3.22 | 39 | 32 | 82 |
| A0301 | 11.9 | 6.48 | 3.23 | 29 | 0 | 0 |
| A1101 | 6.87 | 1.45 | 16.33 | 16 | 1 | 6.2 |
| A2301-05 | 2.5 | 11.77 | 0.8 | 4 | 0 | 0 |
| A2402-07 | 10.3 | 3.14 | 23.97 | 16 | 3 | 18.7 |
| A2501 | 2.12 | 0.45 | 0.46 | 2 | 0 | 0 |
| A2601 | 4.22 | 3.33 | 3.85 | 9 | 4 | 44.4 |
| A2901-02 | 3.01 | 3.94 | 0.86 | 8 | 2 | 25 |
| A3001-10 | 3.39 | 14.48 | 2.1 | 6 | 1 | 16.7 |
| A3101-10 | 2.52 | 1.88 | 4.62 | 7 | 0 | 0 |
| A3201-10 | 3.92 | 2.03 | 0.62 | 10 | 0 | 0 |
| A3301-10 | 2.72 | 5.72 | 5.13 | 9 | 0 | 0 |
| A6801-02 | 3.99 | 9.68 | 1.29 | 6 | 2 | 33 |
| A6901 | 3.99 | 9.68 | 1.29 | 1 | 0 | 0 |
| A7401-09 | | | | 2 | 0 | 0 |
| B0702 | 8.67 | 7.71 | 3.37 | 25 | 25 | 100 |
| B0801 | 7.41 | 4.83 | 1.4 | 22 | 1 | 4.5 |
| B1301-09 | 3.12 | 1.05 | 7.45 | 3 | 0 | 0 |
| B1401-09 | 3.29 | 3.45 | 0.68 | 7 | 0 | 0 |
| B1501-09 | 4.06 | 0.92 | 8.43 | 13 | 0 | 0 |
| B1801-09 | 6.31 | 4.62 | 0.92 | 11 | 1 | 9 |
| B2701-05 | 3.71 | 1.46 | 3.62 | 5 | 2 | 40 |
| B3501-3511 | 10.33 | 5.53 | 5.03 | 19 | 9 | 47.4 |
| B3801 | 2.41 | 0.35 | 2.1 | 5 | 0 | 0 |
| B4001-4006 | 3.12 | 0.45 | 9.03 | 11 | 2 | 18.2 |
| B4201-02 | 0.14 | 5.06 | 0.06 | 3 | 3 | 100 |
| B4401-03 | 11.19 | 5.75 | 3.59 | 22 | 4 | 18.2 |
| DRB1 0301 | 11.1 | 13.99 | 5.02 | 27 | 5 | 18.5 |
| DRB1 0401-04 | 12.82 | 10.51 | 12.99 | 23 | 4 | 17.4 |
| DRB1 0701 | 13.17 | 9.23 | 5.77 | 28 | 3 | 10.7 |
| DRB1 1101-04 | 13.36 | 15.74 | 7.74 | 26 | 8 | 30.8 |
| DRB1 1501-02 | 10.73 | 9.91 | 14.35 | 31 | 5 | 16 |

6.2.2. CMVpp65 Specific T-Cell Responses are Dominated by Epitopes Presented by a Limited Number of HLA Class-I and Class-II Alleles In 103 of the 119 (87%) CTL lines, the immunodominant T-cell responses were restricted by HLA class-I alleles, and in 16 CTL lines, by HLA class-II alleles. In 54% of the CTL lines, the immunodominant T-cell responses were restricted by 3 HLA Class-I alleles; A0201 (25%), B 0702 (21%) and B3501-11 (8%). Other alleles presenting immunodominant epitopes included HLA A 2402, B 4001, B 4006, B 4202, B 4204, B 4402, B 4403, DRB1 0401 and 0404, DRB1 1101, DRB1 1202. Thus, despite the broad array of class-I and class-II HLA alleles represented in this bank, only 19 of these alleles presented epitopes eliciting immunodominant T-cell responses. Furthermore, T-cell responses of any detectable level were specific for epitopes presented by only 49 of the 180 HLA alleles inherited by donors in the bank.

6.2.3. The HLA Alleles Presenting Immunodominant Epitopes Exist in a Hierarchical Order within Individuals Co-Inheriting Specific Haplotypes Evaluation of the T-cell lines in the bank also demonstrated that epitopes presented by specific HLA alleles were consistently dominant, as measured by quantitations of epitope specific IFNγ+ T-cells and ascertainment of their HLA restriction. Previous studies have provided evidence that epitopes of CMVpp65 presented by HLA B0702 are dominant in patients co-inheriting HLA A0201 and B0702 (Lacey, S. F., et al., Hum Immunol, 2003. 64: 440-452). In the series of this example, HLA B0702 was consistently the allele restricting the immunodominant T-cell responses in all 25 donors in the bank inheriting this allele (100%), including 9 that co-inherited HLA A0201. Thus, responses restricted by HLA B0702 were dominant irrespective of the other HLA class-I and class-II alleles inherited.

On the other hand, in 30 of the 39 donors (77%) inheriting HLA A0201, the immunodominant T-cell response was restricted by HLA A0201. The remaining 9 donors were those who co-inherited HLA A0201 and B0702, and in each of these 9 donors, the immunodominant T-cell response was restricted by HLA B 0702. Thus HLA A0201 was the allele restricting the immunodominant T-cell response when co-inherited with any other HLA class-I or class-II alleles, except when co-inherited with HLA B0702. For example, among 22 donors inheriting HLA B44 alleles, only 4 elicited dominant responses restricted by this allele. When these alleles (B4401, B4402, B4403) were co-inherited with HLA A0201, in 11 of 12 such donors (91.6%) the immunodominant CTL responses were restricted by HLA A0201; the other donor also co-inherited HLA B0702 and elicited an HLA B0702 restricted response.

A striking other feature of the T-cell responses in donors inheriting HLA B 0702 or A0201 was the fact that the responses observed were exclusively directed against epitopes presented by these alleles. In contrast, in T cell lines in which responses to immunodominant epitopes were restricted by other HLA alleles, subdominant populations of T-cells specific for other epitopes and restricted by other HLA alleles were commonly observed. This analysis allowed for the recognition of a hierarchical clustering of HLA alleles presenting the immunodominant epitopes as shown in FIG. 1.

The hierarchy of HLA alleles presenting immunodominant epitopes was exclusively based on their level of functional activity in response to peptide stimulation. There was no correlation between the affinity of the peptide for HLA binding and its capacity to elicit immunodominant T-cell responses (Table 2).

TABLE 2

Characterization of HLA alleles presenting immunodominant epitopes.

| No | Epitope | Presenting HLA Allele | Number of CTL Lines Responding | Number of CTL Lines Eptipe Immunodominant | Predicted Binding Score (SYFPEITHI) |
|---|---|---|---|---|---|
| | | HLA Class I | | | |
| 1 | NLVPMVATV | A0201 | 31 | 30 | 30 |
| 2 | TPRVTGGGAM | B0702 | 16 | 13 | 19 |

TABLE 2-continued

Characterization of HLA alleles presenting immunodominant epitopes.

| No | Epitope | Presenting HLA Allele | Number of CTL Lines Responding | Number of CTL Lines Eptipe Immunodominant | Predicted Binding Score (SYFPEITHI) |
|---|---|---|---|---|---|
| 3 | RPHERNGFTV | B0702 | 12 | 7 | 17 |
| 4 | HERNGFTVL | B4001 & 4006, B4201 & 4202, B4403, A2601, A0101 | 11 | 10 | 23 23 23 8 4 |
| 5 | EVQAIRETVE | B3501, B3502, B3503, B3508, B3511 | 7 | 5 | 2 |
| 6 | QYDPVAALF | A2402, 2407 | 5 | 5 | 24 |
| 7 | INVHHYPSAA | A2601 A0101 | 3 1 | 3 1 | 6 0 |
| 8 | YSEHPTFTS | B0801 A0101 | 4 | 3 | 0 13 |
| 9 | QMWQARLTV | B5201 B3502 | 3 1 | 2 1 | not found 1 |
| 10 | VYALPLKMLN | A2402 A6801 B3501 | 1 1 1 | 3 | 14 5 11 |
| 11 | FVFPTKDVAL | A2402 B3501 | 2 2 | 2 2 | 21 13 |
| HLA Class II | | | | | |
| 11 | EHPTFTSQYRIQGKL | DRB1 1101, DRB1 1104, DRB1 1501 | 8 | 7 | 3 3 4 |
| 12 | KYQEFFWDAND | DRB1 1101, DQB1 0501 | 6 | 5 | 1 18 |
| 13 | QPFMRHERNGF | DRB1 0301 DRB1 1501 | 3 | 2 | not found not found |
| HLA class I and Class II (Shared) | | | | | |
| 1 | KYQEFFWDANDIYRI | B1801, DRB1 1101, DQB1 0501 | 1 6 1 | 1 5 0 | not found 1 18 |
| 2 | QIFLEVQAIRETVE | B3501-3511, DRB1 1501 | 7 1 | 5 0 | 2 14 |
| 3 | QPFMRHERNGF | A0101, B0801 DRB1 0301 DRB1 1501 | 1 1 2 1 | 1 1 2 0 | 1 not found not found not found |
| 4 | AGILARNLVPMVATV | A0201 DRB1 0401, DRB1 0402, DRB1 0404 DQB1 0301 | 31 2 1 1 1 | 30 1 1 0 1 | 30 14 14 14 not found |
| 5 | PQYSEHPTFTSQYRI | A0101, B0801 DRB1 0301 | 2 2 2 | 2 2 2 | 13 0 0 |

6.2.4. The Epitope Repertoire and HLA Alleles Constituting the CMV CTL Bank can be Used for Treatment of a Diverse Patient Population A very limited repertoire of immunodominant CMVpp65 epitopes eliciting T-cell responses was discovered within the 119 CTL lines constituting the GMP bank, that were presented by a limited number HLA alleles. Given that T-cell responses are defined by such fine specificity; for antigen specific T-cells to be clinically effective in the third party setting, the T-cells selected would need to be responsive to epitopes presented by an HLA allele shared by the patient. Within these parameters, the proportion of ethnically diverse patients that could potentially be treated using CTLs from this bank was analyzed.

A series of consecutive T-cell depleted transplants performed at the Memorial Sloan-Kattering cancer center over the last 3-5 years from donors that were either HLA matched or HLA mismatched related or unrelated, as well as cord blood donors, was reviewed. In a series of 239 HLA matched related or unrelated transplants at the center, in 86% of such cases a CTL line with a CMV T-cell response restricted by an HLA allele shared with the patient and matching at 1-2 additional HLA alleles was able to be identified. Similarly, in a series of 137 HLA mismatched transplants, and 70 cord blood transplants, an appropriately restricted CTL line in 93% and 81% of the cases respectively was able to be identified. Thus, despite the broad representation of HLA alleles in this CTL bank, T-cells restricted by a limited repertoire of HLA alleles could be identified and used for treatment of most patients in this ethnically diverse group.

6.2.5. Clinical Activity of the CMV CTLs Selected for Treatment from the Transplant Donor or a Third Party Donor Using the Newly Defined Epitope and HLA Restriction Criteria A total of 54 evaluable patients received CMV CTLs as treatment of clinical infection or persistent viremia that had failed to respond to antiviral drugs. Of these 19 received CMVpp65-specific T-cells from their HCT donor (NCTO1646645) and 35 from T-cells from an >2 HLA allele matched third party donor. Results are summarized in Table 3 and Table 4. In this analysis, CR is defined as clearance of clinical infection and/or clearance of detectable CMV from the blood. PR is defined as a reduction of CMV in the blood >2 log 10. SD is defined as patients with stable clinical status and a reduction of CMV of <2 log 10. POD is defined as continued progression of viremia and clinical disease.

TABLE 3

Responses by HLA restriction of CMVpp65-specific T-cells administered.

| RESTRICTING HLA OF T-CELLS (EPITOPE) | N TREATED AND EVALUABLE | RESPONSES | | | |
|---|---|---|---|---|---|
| | | CR | PR | SD | POD |
| HLA-A0201 (NLVPMVATV) | 19 | 12 | 2 | 3 | 2 |
| HLA-B0702 (TPRVTGGGAM or RPHERNGFTV) | 8 | 8 | 0 | 0 | 0 |
| HLA-B0801 (DVEEDLTMT) | 3 | 3 | 0 | 0 | 0 |
| HLA B4401-3/B4001 (HERNGFTVL) | 5 | 2 | 1 | 1 | 0 |
| HLA-B3501 (N = 3) (IPSINVHHY) HLA-B3502 (N = 3) (QMQARLTVS) HLA-B3508 (N = 1) (EVQAIRETVE) | 7 | 0 | 0 | 0 | 7 |
| HLA-A2601 (INVHHYPSAA) | 3 | 0 | 0 | 0 | 3 |

TABLE 4

Immunodominant HLA alleles detected in other CMVpp65 specific T-cells administered

| HLA Allele Restriction (Epitope) | N Evaluable | Response | | | |
|---|---|---|---|---|---|
| | | CR | PR | SD | POD |
| A2407 (QYDPVAALF) | 1 | 0 | 0 | 0 | 1 |
| A2902 (VCSMENTRAT) | 1 | 1 | 0 | 0 | 0 |
| A3001 (RVSQPSLIL) | 1 | 0 | 1 | 0 | 0 |
| B0705 (GVMTRGRLKA) | 1 | 1 | 0 | 0 | 0 |
| B1801 (KYQEFFWDAN) | 1 | 0 | 1 | 0 | 0 |
| B2704 (VSVNVHNPT) | 1 | 1 | 0 | 0 | 0 |
| DRB1 0301 (QPFMRPHERNG) | 1 | 0 | 0 | 0 | 1 |
| DRB1 0701 (SGKLFMHVTLG) | 1 | 0 | 0 | 0 | 1 |
| DRB1 1101 (FTSQYRIQGKL) | 1 | 0 | 1 | 0 | 0 |

As can be seen, of 19 patients who received T-cells specific for a CMVpp65 epitope presented by HLA A201, 14 achieved a CR or PR. Of 9 treated with T-cells specific for an immunodominant epitope presented by HLA B0702, 8 achieved a CR. Similarly, immunodominant T-cells restricted by HLA A2402 (N=2) and B0801 (N=3) induced CRs in each of the 5 cases treated.

In contrast, 7/7 recipients of CMVpp65-specific T-cells specific for an immunodominant epitope presented by an allelic variant of HLA B35 failed to respond. Similarly, immunodominant T-cells specific for epitopes of A2601 (N=3), A2407 (N=1) and B5001 (N=1) failed to clear infection or reduce viremia.

These prospective results provide evidence that immunodominant epitopes presented by specific HLA alleles induce T-cells that had better therapeutic activity in vivo.

The patients who received transplants from the donors who also agreed to have their CMVpp65-specific T-cells included in the bank for use in individuals other than to whom they also donated an HLA compatible HCT were also retrospectively examined. The reason was that T-cell depleted transplants from such donors, which usually contain $2-8 \times 10^3$ T-cells/Kg recipient weight, would also provide small numbers of immunodominant CMV-specific T-cells, since the frequency of IFNγ+ CMV specific T-cells in the blood in seropositive donors was in the range of 0.1-1% of the circulating T-cells. The results of this initial analysis are presented in Table 5.

TABLE 5

Analysis of CMV reactivation, disease and ultimate response to CMV-directed therapy in patients who received transplants from HLA compatible donors who also contributed cells for the bank as third party donors.

| HLA Allele | N | No | Level of CMV Reactivation Low (2-13/Slide ≤1000) | Level of CMV Reactivation High (≥100/slide >slide) | CMV Disease | Rx T-Cells | Type of Disease | Ult. No Response |
|---|---|---|---|---|---|---|---|---|
| B0702 | 25 | 9 | 7 | 9 | 0 | 6 | — | 0 |
| A0201 | 36 | 14 | 12 | 10 | 1 | 7 | BAL + L.P. | 0 |
| No B0702 | 29 | 11 | 12 | 6 | 1 | — | BAL + L.P. | |
| B0801 No B0702 | 16 | 8 | 4 | 4 | 1 | — | Other | 0 |
| B35 No A02 or B07 | 13 | 2 | 3 | 8 | 7 | — | 1 Meningoma 1 Hepatitis 3 Pneumonia 2 Other | 6 |
| A1101 No A02 or B7 | 13 | 4 | 2 | 7 | 2 | — | 1 Pneumonia 1 Colitis | 2 |
| A2601 | 9 | 3 | 3 | 3 | 3 | — | 2 Other 1 Pneumonia | 1 |
| A0101 No A2 or B7 | 16 | 9 | 3 | 4 | 3 | — | 1 Meningoma 1 Other 1 Pneumonia | 2 |
| A2402 No A2 or B7 | 13 | 5 | 3 | 5 | 2 | — | 1 Pneumonia | 1 |
| A0301 No A2 or B7 | 8 | 3 | 2 | 3 | 1 | — | 1 CSF+ | 0 |

Again, as seen in the patients treated with CMVpp65-specific T-cells, recipients of transplants from donors sharing the HLA B0702 and A0201 alleles had a low risk of developing CMV disease, and virema consistently responded to treatment, while those who received grafts from donors lacking these alleles, had a significant incidence of overt infection. This was again particularly observed in patients bearing variants of HLA B35 who lacked either HLA B0702 or A0201.

The clinical data permitted us to determine a hierarchy of certain HLA alleles presenting immunodominant epitopes of CMVpp65 eliciting peptide-specific T cell responses (see Table 6), an example of a Representation of Activity.

TABLE 6

Hierarchy of HLA alleles presenting immunodominant epitopes of CMVpp65 eliciting peptide-specific T cell responses.

| RESTRICTING HLA OF T CELL LINE | RANK[a] |
|---|---|
| HLA-B0702 | 1 |
| HLA-A0201 | 2 |
| HLA-B0801 | 3 |
| HLA-B4401 | 4 |

[a]A higher rank corresponds to greater clinical effectiveness of the T cell line restricted by the HLA allele in treatment of patients having CMV infection or persistent viremia who failed to respond to antiviral drugs Our data indicated that HLA-B35 variants should not be used (and thus would be deemed "disqualified" from among the HLA alleles in the representation).

6.3. The Data Suggests that:

1. A limited repertoire of CMVpp65 epitopes elicit functional CMV specific cytotoxic T-cell responses and a total of 49 HLA alleles out of 181 alleles represented within this CTL bank present these immunodominant CMVpp65 epitopes.

2. The identified peptide epitopes could be used for the development of an effective polypeptide vaccine, or used as a limited peptide pool for generation of highly functional CMV CTLs in the future for adoptive immunotherapy.

3. Incorporating the analysis of HLA hierarchy in the selection of CTL lines for treatment should promote higher and more consistent efficacy of third party CTL treatment.

6.4. Summary of Clinical and Experimental Findings

Adoptively transferred virus-specific T-cells, to be effective, must be specific for a viral peptide epitope that is both expressed by host cells infected by the virus and presented by an HLA allele expressed by the infected host cells and the donor T-cells through which the HLA-restricted donor T-cells recognize the viral epitope.

Following resolution of primary infection with CMV, the initially broad repertoire of responding T-cells contracts, such that T-cells specific for only a limited number of immunodominant epitopes are sustained. As a result, CMVpp65-specific T-cell lines expanded from latently infected, CMV seropositive normal donors are usually specific for only 1-2 immunodominant CMVpp65 peptides presented by only 1-2 HLA alleles expressed by the donor.

We have found that there is a hierarchy of HLA alleles presenting immunodominant epitopes of CMVpp65 eliciting peptide-specific T-cell responses, that leads to preferential expansion of CMVpp65-specific T-cells presented by specific HLA alleles over all others inherited and expressed. This hierarchy is not based on the binding affinity of the peptide to the presenting allele. As a result of this hierarchy of HLA restriction:

1. The immunodominant epitopes eliciting CMVpp65-specific T-cells detected in in vitro expanded T-cell lines are presented by only a limited number of HLA alleles.

2. Furthermore, among individuals inheriting two or more HLA alleles from this limited repertoire of HLA alleles that present immunodominant peptide epitopes, certain HLA alleles (e.g. HLA B0702 or HLA A0201) consistently present the epitopes that elicit responses to the exclusion of the others.

Early results of phase II trials further indicate that, for patients with CMV infection or persistent viremia that have failed antiviral drug therapy who are then treated with third party donor-derived CMVpp65-specific T-cells that are restricted by an HLA allele expressed by infected cells in the host, those patients receiving CMVpp65-specific T-cells that are restricted by the same top HLA alleles in the hierarchy (e.g. HLA B0702, or HLA A0201) consistently respond while treatment with CMVpp65-specific T-cells restricted by HLA alleles lower in the hierarchy can clear infection, responses are less consistent.

7. INCORPORATION BY REFERENCE

Various publications are cited herein, the disclosures of which are hereby incorporated by reference herein in their entireties.

What is claimed is:

1. A method of selecting an allogeneic T cell line for therapeutic administration to a human patient having or suspected of having a pathogen or cancer, comprising:
   (a) selecting a T cell line allogeneic to the patient that recognizes at least one epitope of an antigen of the pathogen or the cancer, using a representation that (i) identifies a plurality of HLA alleles and optionally HLA allele combinations, and (ii) discloses indications of relative activities of T cell lines, each recognizing at least one epitope of an antigen of the pathogen or cancer, and restricted to different ones of the HLA alleles or HLA allele combinations in the plurality; wherein in the representation each identified HLA allele or HLA allele combination is associated with the respective indication of relative activity of the T cell line restricted to the HLA allele or HLA allele combination, the relative activities being relative measures of known activity against the pathogen or against the cancer exhibited by the T cell lines, wherein the relative activities are in vivo clinical efficacies of the T cell lines in treatment of human patients having the pathogen or cancer, wherein each indication of relative activity is based on clinical data from a population of human patients; wherein
   (A) the T cell line selected has in common with the patient or diseased cells in the patient the HLA allele or HLA allele combination identified by the representation to which the recognition of the T cell line is restricted; and
   (B) the HLA allele or HLA allele combination, to which the T cell line selected is restricted, is associated in the representation with an indication of the highest relative activity among the HLA alleles and HLA allele combinations in the representation that are known to be in common with the patient or the diseased cells in the patient and are not otherwise disqualified;
   (b) generating the representation prior to the selecting step; and
   (c) measuring the relative activities prior to the generating step.

2. The method of claim 1, wherein the representation is a list of the plurality of HLA alleles and optionally HLA allele combinations ranked by the relative activities.

3. The method of claim 1, wherein the representation is a database listing the plurality of HLA alleles and optionally HLA allele combinations, each associated with a score indicative of relative activity.

4. The method of claim 1, wherein the patient has or is suspected of having a pathogen, wherein the T cell lines recognize at least one epitope of an antigen of the pathogen, and wherein the relative activities are relative measures of known activity against the pathogen.

5. The method of claim 4, wherein the pathogen is a virus.

6. The method of claim 5, wherein the virus is CMV.

7. The method of claim 6, wherein the patient has or is suspected of having a CMV infection subsequent to the patient having undergone a hematopoietic stem cell transplant.

8. The method of claim 6, wherein the antigen is CMV pp65.

9. The method of claim 5, wherein the virus is EBV.

10. The method of claim 1, wherein the patient has or is suspected of having a cancer, wherein the T cell line recognizes at least one epitope of an antigen of the cancer, and wherein the relative activities are relative measures of known activity against the cancer.

11. The method of claim 10, wherein the antigen is WT1.

12. The method of claim 10, wherein the cancer is a lymphoproliferative disorder.

13. The method of claim 12, wherein the cancer is an EBV-positive post-transplant lymphoproliferative disorder.

14. The method of claim 13, wherein the antigen is EBNA1, EBNA2, EBNA3A, EBNA3B, EBNA3C, LMP1 or LMP2.

15. The method of claim 10, wherein the cancer is an EBV-positive nasopharyngeal carcinoma.

16. The method of claim 15, wherein the antigen is EBNA1, LMP1, or LMP2.

17. The method of claim 10, wherein the cancer is a cancer of the blood, breast, lung, ovary, stomach, pancreas, larynx, esophagus, testes, liver, parotid, biliary tract, colon, rectum, cervix, uterus, endometrium, kidney, bladder, prostate, thyroid, brain or skin.

* * * * *